US012678224B2

(12) United States Patent
Wong et al.

(10) Patent No.: US 12,678,224 B2
(45) Date of Patent: Jul. 14, 2026

(54) FLEXIBLE INSTRUMENTS WITH PATTERNED ANTENNA ASSEMBLIES HAVING VARIABLE RECOVERABLE FLEXIBILITY

(71) Applicant: INTUITIVE SURGICAL OPERATIONS, INC., Sunnyvale, CA (US)

(72) Inventors: Serena H. Wong, Los Altos, CA (US); Samuel Raybin, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 731 days.

(21) Appl. No.: 17/917,881

(22) PCT Filed: Apr. 6, 2021

(86) PCT No.: PCT/US2021/026040
§ 371 (c)(1),
(2) Date: Oct. 7, 2022

(87) PCT Pub. No.: WO2021/207264
PCT Pub. Date: Oct. 14, 2021

(65) Prior Publication Data
US 2023/0149080 A1 May 18, 2023

Related U.S. Application Data

(60) Provisional application No. 63/028,928, filed on May 22, 2020, provisional application No. 63/008,615, filed on Apr. 10, 2020.

(51) Int. Cl.
*A61B 18/18* (2006.01)
*A61B 18/00* (2006.01)

(52) U.S. Cl.
CPC ..................... *A61B 18/1815* (2013.01); *A61B 2018/00577* (2013.01); *A61B 2018/1892* (2013.01)

(58) Field of Classification Search
CPC ................ A61B 18/18; A61B 18/1815; A61B 2018/1892; A61B 2018/00577;
(Continued)

(56) References Cited

U.S. PATENT DOCUMENTS 6,036,687 A * 3/2000 Laufer .................. A61B 18/08
604/113
6,380,732 B1 4/2002 Gilboa
(Continued)

FOREIGN PATENT DOCUMENTS

CA 2904190 A1 9/2014
WO WO-2010081062 A1 7/2010
WO WO-2019191415 A1 10/2019

OTHER PUBLICATIONS

International Preliminary Report on Patentability for Application No. PCT/US2021/026040 mailed Oct. 20, 2022, 10 pages.
(Continued)

*Primary Examiner* — Thomas A Giuliani
(74) *Attorney, Agent, or Firm* — Haynes & Boone, LLP

(57) ABSTRACT

Flexible instruments and associated systems and methods are disclosed herein. In some embodiments, a flexible instrument comprises an elongate device having an inner conductor, an outer conductor surrounding the inner conductor, and a dielectric layer insulating the inner conductor from the outer conductor. The flexible instrument further includes a recess formed in the outer conductor. An insert is positioned within the recess and about the inner conductor.

20 Claims, 10 Drawing Sheets

(58) Field of Classification Search
CPC .... A61B 2018/1846; A61B 2018/1853; A61B
2018/1861; A61B 2018/1869; A61B
2018/1838; A61B 2018/1876
USPC .................... 606/33; 607/100, 101, 154–156
See application file for complete search history.

(56) References Cited

U.S. PATENT DOCUMENTS

| | | | |
|---|---|---|---|
| 6,389,187 B1 | 5/2002 | Greenaway et al. | |
| 7,316,681 B2 | 1/2008 | Madhani et al. | |
| 7,772,541 B2 | 8/2010 | Froggatt et al. | |
| 7,781,724 B2 | 8/2010 | Childers et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 10,188,460 B2 | 1/2019 | Brannan et al. | |
| 10,314,652 B2 | 6/2019 | Brannan | |
| 2003/0088242 A1* | 5/2003 | Prakash | A61B 18/18 606/33 |
| 2003/0100894 A1* | 5/2003 | Mahon | A61B 18/1815 606/41 |
| 2007/0233057 A1* | 10/2007 | Konishi | A61B 18/1477 607/156 |
| 2011/0060325 A1* | 3/2011 | Bonn | H01Q 9/30 333/24 R |
| 2013/0116679 A1* | 5/2013 | Van Der Weide | A61B 17/320068 606/33 |
| 2013/0304057 A1* | 11/2013 | Rossetto | A61B 18/1815 606/33 |
| 2019/0069951 A1 | 3/2019 | Hancock et al. | |
| 2019/0275260 A1 | 9/2019 | Ralph et al. | |
| 2020/0138514 A1 | 5/2020 | Blumenkranz et al. | |
| 2020/0138515 A1 | 5/2020 | Wong | |
| 2020/0142013 A1 | 5/2020 | Wong | |

OTHER PUBLICATIONS

International Search Report and Written Opinion for Application No. PCT/US2021/026040, mailed on Nov. 29, 2021, 21 pages.
Invitation to pay additional fee received from the International Search Authority for Application No. PCT/US2021/026040, mailed Aug. 18, 2021, 13 pages.
Malhotra, N., et al., "Reconfigurable Tapered Coaxial Slot Antenna for Hepatic Microwave Ablation," Electromagnetic Biology and Medicine, 2016, vol. 35 (3), pp. 214-221.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Zafar, T., et al., "Development and Microwave Analysis of Slot Antennas for Localized Hyperthermia Treatment of Hepatocellular Liver Tumor" Australasian Physical & Engineering Sciences in Medicine, Dec. 2014, vol. 37 (4), pp. 673-679.

* cited by examiner

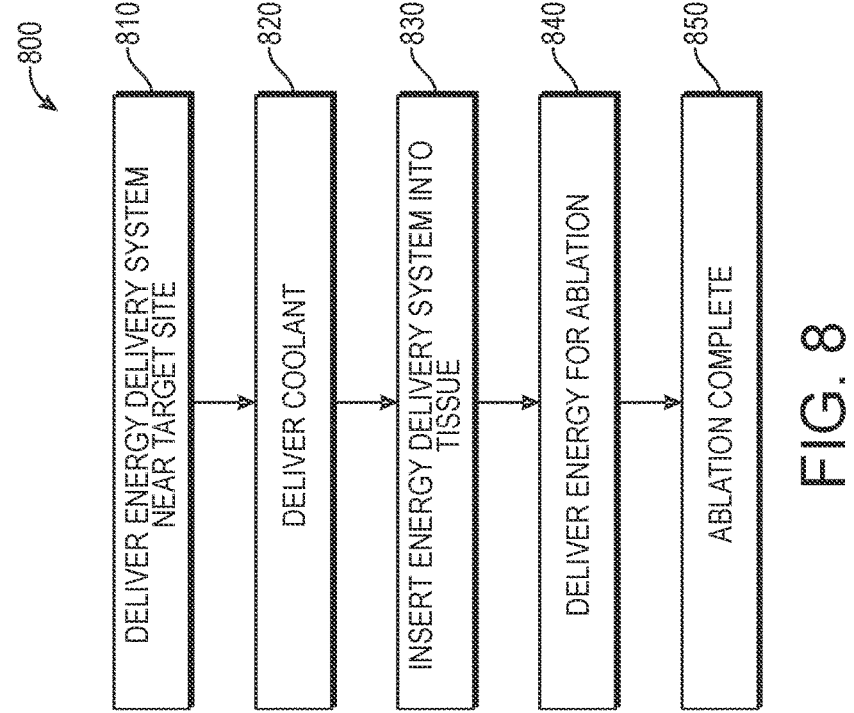

800

810  DELIVER ENERGY DELIVERY SYSTEM NEAR TARGET SITE

820  DELIVER COOLANT

830  INSERT ENERGY DELIVERY SYSTEM INTO TISSUE

840  DELIVER ENERGY FOR ABLATION

850  ABLATION COMPLETE

FIG. 8

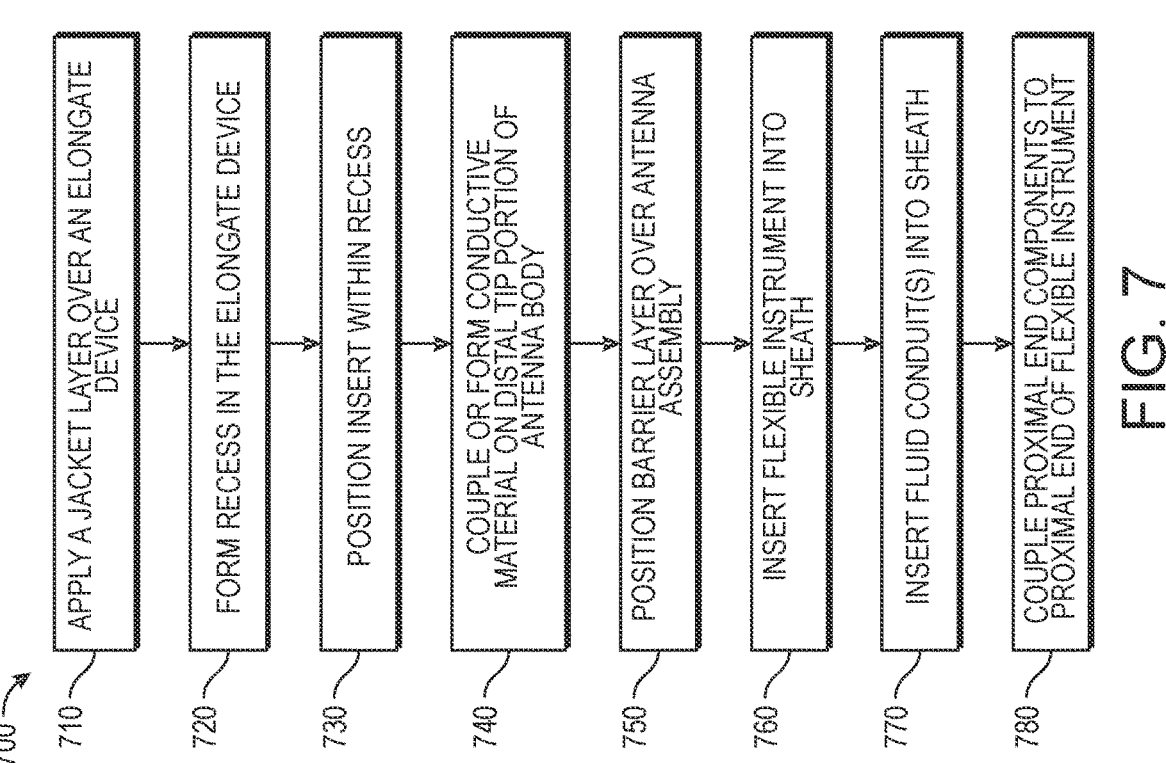

700

710  APPLY A JACKET LAYER OVER AN ELONGATE DEVICE

720  FORM RECESS IN THE ELONGATE DEVICE

730  POSITION INSERT WITHIN RECESS

740  COUPLE OR FORM CONDUCTIVE MATERIAL ON DISTAL TIP PORTION OF ANTENNA BODY

750  POSITION BARRIER LAYER OVER ANTENNA ASSEMBLY

760  INSERT FLEXIBLE INSTRUMENT INTO SHEATH

770  INSERT FLUID CONDUIT(S) INTO SHEATH

780  COUPLE PROXIMAL END COMPONENTS TO PROXIMAL END OF FLEXIBLE INSTRUMENT

FIG. 7

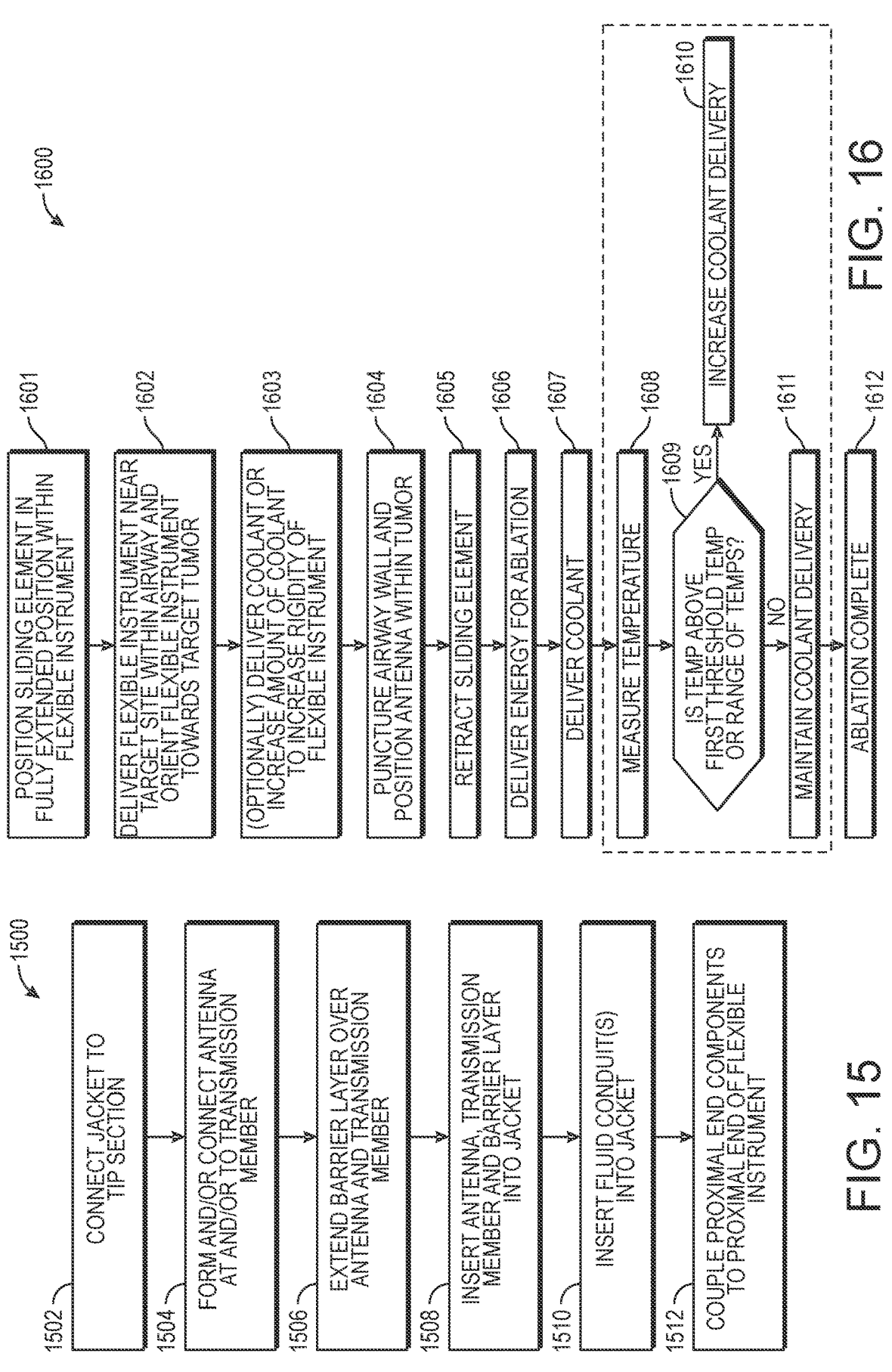

1601 — POSITION SLIDING ELEMENT IN FULLY EXTENDED POSITION WITHIN FLEXIBLE INSTRUMENT

1602 — DELIVER FLEXIBLE INSTRUMENT NEAR TARGET SITE WITHIN AIRWAY AND ORIENT FLEXIBLE INSTRUMENT TOWARDS TARGET TUMOR

1603 — (OPTIONALLY) DELIVER COOLANT OR INCREASE AMOUNT OF COOLANT TO INCREASE RIGIDITY OF FLEXIBLE INSTRUMENT

1604 — PUNCTURE AIRWAY WALL AND POSITION ANTENNA WITHIN TUMOR

1605 — RETRACT SLIDING ELEMENT

1606 — DELIVER ENERGY FOR ABLATION

1607 — DELIVER COOLANT

1608 — MEASURE TEMPERATURE

1609 — IS TEMP ABOVE FIRST THRESHOLD TEMP OR RANGE OF TEMPS?

YES

1610 — INCREASE COOLANT DELIVERY

NO

1611 — MAINTAIN COOLANT DELIVERY

1612 — ABLATION COMPLETE

1502 — CONNECT JACKET TO TIP SECTION

1504 — FORM AND/OR CONNECT ANTENNA AT AND/OR TO TRANSMISSION MEMBER

1506 — EXTEND BARRIER LAYER OVER ANTENNA AND TRANSMISSION MEMBER

1508 — INSERT ANTENNA, TRANSMISSION MEMBER AND BARRIER LAYER INTO JACKET

1510 — INSERT FLUID CONDUIT(S) INTO JACKET

1512 — COUPLE PROXIMAL END COMPONENTS TO PROXIMAL END OF FLEXIBLE INSTRUMENT

FLEXIBLE INSTRUMENTS WITH PATTERNED ANTENNA ASSEMBLIES HAVING VARIABLE RECOVERABLE FLEXIBILITY

CROSS-REFERENCE TO RELATED APPLICATION(S)

The present application is the U.S. National Stage patent application of International Patent Application No. PCT/US2021/026040, filed Apr. 6, 2021 which claims priority to the following pending applications:

U.S. Provisional Patent Application No. 63/008,615, filed Apr. 10, 2020; and

U.S. Provisional Patent Application No. 63/028,928, filed May 22, 2020.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present disclosure is directed to minimally invasive ablation devices and systems and associated methods of use.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include ablation instruments. Ablation instruments transmit energy, e.g., in the form of electromagnetic waves to a targeted area of tissue, such as a tumor or other growth, within the patient anatomy to destroy the targeted tissue. Some minimally invasive medical tools and ablation instruments may be teleoperated or otherwise computer-assisted or delivered by a teleoperated, robotic, or otherwise computer-assisted system. Various features may improve the effectiveness of minimally invasive ablation instruments.

SUMMARY

Embodiments of the present technology are best summarized by the claims that follow the description.

In some embodiments, a flexible instrument comprises an elongate device including an inner conductor, an outer conductor surrounding the inner conductor, and a dielectric layer insulating the inner conductor from the outer conductor. The flexible instrument also includes a recess formed in the outer conductor. An insert is positioned within the recess and about the inner conductor.

In some embodiments, an energy delivery system comprises a flexible instrument. The flexible instrument includes a transmission member, an antenna at a distal end of the transmission member, a sheath surrounding the antenna and the transmission member, and at least one fluid conduit at least partially disposed within the sheath. The at least one fluid conduit defines a fluid inlet channel configured to transport fluid proximal to a distal end of the antenna. Additionally, the at least one fluid conduit is configured to provide variable recoverable flexibility along at least a section of the flexible instrument. The at least one fluid conduit is further composed of a material that prevents interference of energy delivery by the antenna.

In these and other embodiments, an energy delivery system comprises a flexible instrument and a fluid conduit. The flexible instrument includes a transmission member, an antenna at a distal end of the transmission member, and a sheath surrounding the transmission member and the antenna. The fluid conduit is at least partially disposed within the sheath. The sheath defines a fluid channel surrounding at least a distal end portion of the antenna. The energy delivery system further comprises a translation actuator to alter the state of the fluid conduit from a first state to a second state. The first state includes an extended position overlapping the antenna with the fluid conduit. The second state includes a retracted position not overlapping the antenna with the fluid conduit.

In these and other embodiments, a method of operating an energy delivery system comprises (i) providing resilient flexibility and (ii) delivering energy. The energy delivery system includes a flexible instrument having a transmission member, an antenna at a distal end of the transmission member, a sheath surrounding the flexible instrument, and a sliding element at least partially disposed within the sheath. Providing resilient flexibility includes providing resilient flexibility using the sliding element while the sliding element is positioned to overlap with at least a section of the antenna during navigation of the flexible antenna to a target within a subject. Delivering energy to the target includes delivering energy to the target via the antenna while the sliding element is positioned proximal to the antenna.

In these and still other embodiments, a method of operating an energy delivery system comprises (i) providing resilient flexibility and (ii) delivering fluid. The energy delivery system includes a flexible instrument having a transmission member, an antenna at a distal end portion of the transmission member, a sheath surrounding the flexible instrument, and a fluid conduit at least partially disposed within the sheath. Providing resilient flexibility includes providing resilient flexibility, using the fluid conduit, to at least a section of the flexible instrument during navigation of the flexible instrument through patient anatomy to a target within a patient. Delivering fluid includes delivering fluid proximate the antenna at least while delivering energy to the target via the antenna. The fluid is delivered via the fluid conduit while a distal end portion of the fluid conduit is extended to a distal end portion of the antenna.

In these and other embodiments, an energy delivery system comprises a flexible instrument having an elongate device with an inner conductor, an outer conductor surrounding the inner conductor, and a dielectric layer insulating the inner conductor from the outer conductor. The flexible instrument further includes a recess formed in the outer conductor and an insert disposed within the recess and about the inner conductor. The energy delivery system also comprises a sheath surrounding the flexible instrument and at least one fluid conduit at least partially disposed within the sheath and extending along the flexible instrument. The at least one fluid conduit defines a fluid inlet channel configured to transport fluid to a distal end region of the flexible instrument, and further provides variable recoverable flexibility along at least a portion of the flexible instrument.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

FIG. 7 is a flow diagram illustrating a method for manufacturing an energy delivery system in accordance with an embodiment of the present technology.

FIG. 8 is a flow diagram illustrating a method of operating an energy delivery system in accordance with an embodiment of the present technology.

FIG. 15 is a flow diagram illustrating a method of operating an energy delivery system in accordance with various embodiments of the present technology.

FIG. 16 is a flow diagram illustrating a method for manufacturing an energy delivery system in accordance with various embodiments of the present technology.

DETAILED DESCRIPTION

Figures 1, 2:
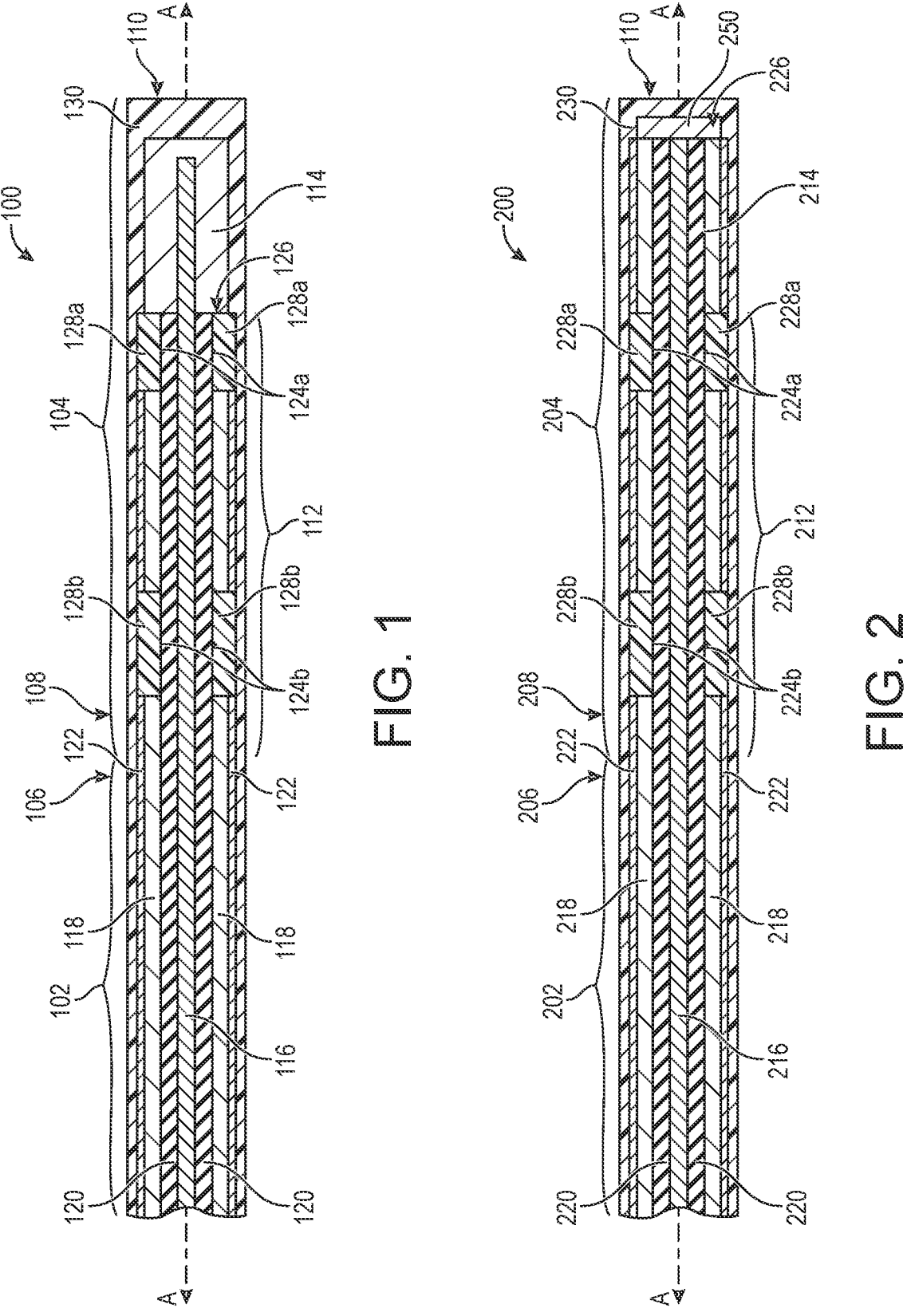
FIG. 1 is a side cross-sectional view of a flexible instrument for tissue ablation configured in accordance with an embodiment of the present technology.
FIG. 2 is a side cross-sectional view of a flexible instrument for tissue ablation configured in accordance with another embodiment of the present technology.

The present disclosure is directed to energy delivery systems including minimally invasive ablation devices and systems (and associated methods). The energy delivery systems are used for tissue ablation, causing an increase in temperature of an anatomic target area by transmitting electromagnetic waves from the energy delivery system to the anatomic target area or ablation site. In some embodiments, an energy delivery system includes a flexible instrument having a transmission member and an antenna assembly extending from a distal end portion of the transmission member. The transmission member and antenna assembly can be formed from an elongate device (such as a coaxial cable) having an inner conductor, an outer conductor, and an insulating layer electrically separating the inner and outer conductors. The antenna assembly can be patterned with one or more recesses formed in the outer conductor to modify the field pattern of electromagnetic energy used to affect tissue.

To prevent excessive heating that may cause unwanted damage to patient tissue, energy delivery systems configured in accordance with the present technology may be cooled by a coolant (e.g., a fluid or gas). Thus, in some embodiments, an energy delivery system includes a fluid cooling system and a flexible instrument. The flexible instrument includes (i) a transmission member, (ii) an antenna extending from a distal end of the transmission member, and (iii) one or more fluid conduits. The transmission member, the antenna, and the one or more fluid conduits are disposed within a sheath. A fluid channel is formed between the sheath and at least a portion of the antenna.

To facilitate delivery of the flexible instrument to a target site within patient anatomy, the flexible instrument must be sufficiently flexible to undergo substantial deformation while navigating patient anatomy, yet axially rigid and stiff enough to puncture tissue without buckling or kinking. Additionally, the distal section of the flexible instrument must be resilient enough to return (e.g., recover, spring back, etc.) to an initial (e.g., undeformed) state or shape after being deformed (e.g., to reduce navigational error and/or align the flexible instrument with a desired axis before performing a puncture operation). Flexible coaxial cables having a multi-filament outer conductor layer (e.g., a braided or wrapped layer) are generally more deformable compared to semi-rigid coaxial cables having a solid outer conductor layer, and may therefore be more suitable for navigation through tortuous patient anatomy (e.g., the airways of the lungs).

However, it may be more difficult to form recesses in a flexible coaxial cable because the multi-filament outer conductor layer tends to unravel or fray when cut. Additionally, the exposed inner conductor and insulating layer may be mechanically weak, which may increase the likelihood of mechanical failure when the flexible instrument is bent, make it more difficult to insert the flexible instrument into tissue, reduce recoverability, etc. Moreover, conventional coaxial cables may include a thick layer of material over the outer conductor, which may reduce the deformability of the flexible instrument, prevent the flexible instrument from being introduced into narrow passages, and/or interfere with coolant flow around the flexible instrument.

Accordingly, to overcome these and other challenges, the flexible instruments described herein may be reinforced at or near the location of the recess in the outer conductor. In some embodiments, for example, an insert made of a non-conductive material (e.g., plastic, adhesive, filler, etc.) is positioned within the recess to protect and provide mechanical support to the corresponding portions of the insulator layer and inner conductor. This non-conductive material is preferably something with low RF loss and can withstand the temperatures needed for ablation (such as polytetrafluoroethylene (PTFE), polyetheretherketone (PEEK), etc.). Additionally, an intermediate layer (e.g., a jacket layer or coax jacket layer) can be positioned over at least a portion of the outer conductor to reduce or prevent unraveling at the recess. The intermediate layer can be made of a material (e.g., fluoropolymers including ethylene tetrafluoroethylene (ETFE) or PEEK, plastic, polyethylene terephthalate (PET) coating, heat-shrink, etc.) that also provides mechanical support, axial rigidity, and/or recoverability to the flexible instrument. The intermediate layer may be composed a non-conductive material or a partially conductive material (depending upon positioning relative to the antenna assembly). The intermediate layer can be thin enough to avoid interference with coolant flow and permit the flexible instrument to be navigated within narrow and/or tortuous anatomic passageways.

As noted previously, in some embodiments, the energy delivery systems described herein include one or more fluid conduits for delivering coolant to the flexible instrument. The fluid conduit(s) may extend to at least a distal end portion of the antenna assembly to provide recoverable flexibility and support along a maximized length of the flexible instrument, as well as an added benefit of delivering coolant to the distal end portion of the antenna assembly for increased and/or more uniform cooling of the antenna assembly. However, many shape memory and other resiliently flexible materials (including nitinol) are conductive at the microwave frequency range (e.g., 300 megahertz (MHz) to 300 gigahertz (GHz) of the antenna assembly, meaning that any region of the fluid conduit that runs alongside the antenna assembly and is formed of a conductive material would interfere with the antenna assembly during energy delivery. Accordingly, the region of the fluid conduit that runs alongside the antenna assembly can be formed of a plastic, polymer, or other non-conductive material that does not interfere with the antenna assembly during energy delivery; and/or the conductive, shape-memory region of the fluid conduit can be variably positioned such that the conductive material is not positioned alongside the antenna assembly during energy delivery.

Resiliently flexible materials, such as nitinol or other shape memory materials, are often expensive relative to other materials. Moreover, a proximal section of the flexible instrument typically does not undergo the extent of deformation experienced by the distal section of the flexible instrument. As such, recoverable flexibility can be less of a concern along the proximal section than the distal section of the flexible instrument. Thus, in some embodiments, the fluid conduits can include a region that can be formed of a less expensive material (e.g., stainless steel, PEEK, or other metals and plastics) and that can run along at least a portion of the proximal section of the flexible instrument.

Specific details of several embodiments of the present technology are described herein with reference to FIGS. 1-18B. Although many of the embodiments are described below in the context of navigating and performing medical procedures within lungs of a patient, other applications and other embodiments in addition to those described herein are within the scope of the present technology. For example, unless otherwise specified or made clear from context, the devices, systems, and methods of the present technology can be used for navigating and performing medical procedures on, in, or adjacent other patient anatomy, such as the bladder, urinary tract, GI system, and/or heart of a patient.

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

As used herein, the term "operator" shall be understood to include any type of personnel who may be performing or assisting a procedure and, thus, is inclusive of a physician, a surgeon, a doctor, a nurse, a medical technician, other personnel or user of the technology disclosed herein, and any combination thereof. As used herein, the term "patient" should be considered to include human and/or non-human (e.g., animal) patients upon which a medical procedure is being performed.

FIGS. 1-5 illustrate various embodiments of flexible instruments and energy delivery systems. In some embodiments, the energy delivery systems are used for tissue ablation, such as by causing an increase in temperature of an anatomic target area by transmitting electromagnetic waves from an antenna assembly to the anatomic target area or ablation site. As described in greater detail below, the antenna assembly can be sufficiently flexible to allow for navigation through tortuous passages in the target area, while also having sufficient mechanical strength and structural integrity to withstand deformation (e.g., bending) and/ or insertion into tissue without mechanical failure (e.g., buckling, kinking). To prevent excessive heating that may cause unwanted damage to patient tissue, the energy delivery system can be cooled by a coolant (e.g., a fluid, liquid, or gas) as disclosed in the following embodiments. In some embodiments, the energy delivery systems may be suitable for use in, for example, surgical, diagnostic, therapeutic, ablative, and/or biopsy procedures. In some embodiments, the energy delivery systems may be used as a medical instrument in procedures performed with a teleoperated medical system, as described in further detail below. While some embodiments are provided herein with respect to such procedures, any reference to medical or surgical instruments and medical or surgical methods is non-limiting. In some embodiments, the energy delivery systems may be used for non-teleoperational or non-robotic procedures involving traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

FIG. 1 is a side cross-sectional view of a flexible instrument 100 for tissue ablation configured in accordance with an embodiment of the present technology. As shown in FIG. 1, the flexible instrument 100 includes a transmission member 102 and an antenna assembly 104. The transmission member 102 can be an elongate structure having a proximal end (not shown) and a distal portion 106. The antenna assembly 104 is located at the distal portion 106 of the transmission member 102, and extends distally from transmission member 102 between a proximal portion 108 and a distal tip 110 of the antenna assembly 104.

The transmission member 102 is configured to conduct energy from a proximal energy source (not shown) to the antenna assembly 104. As described in greater detail below, the antenna assembly 104 is used to radiate energy (e.g., microwave energy) for use in the tissue ablation process. In some embodiments, the antenna assembly 104 is used to create electromagnetic radiation within a wavelength range of one meter to one millimeter, and within a frequency range of approximately 300 MHz to 300 GHz (e.g., a microwave). A microwave, which is a type of radio wave, is made up of a magnetic field at a right angle to an electric field, and both the magnetic field and the electric field oscillate at a specific frequency and travel together along a direction that is perpendicular to both the magnetic field and the electric field. In some embodiments, the wavelength and the frequency of the microwaves being radiated by the antenna assembly 104 may be modified to cause a desired type of ablation at the ablation target site. As described in greater detail below, the antenna assembly 104 can include an antenna body 112, and optionally a cap structure 114, having features configured to generate a desired energy radiation pattern for ablation.

In some embodiments, the transmission member 102 and the antenna body 112 are formed from an elongate device such as a coaxial cable (e.g., a flexible coaxial cable). The transmission member 102 and antenna body 112 can be integrally formed from a single elongate device, e.g. coaxial cable, such that a proximal section of the elongate device forms the transmission member 102 and a distal section of the elongate device forms the antenna body 112. The elongate device can have an inner conductor 116, an outer conductor 118 at least partially surrounding the inner conductor 116, and at least one insulating layer 120 between the inner conductor 116 and the outer conductor 118. The insulating layer 120 can at least partially surround the inner conductor 116 to insulate and electrically separate the inner conductor 116 from the outer conductor 118. The inner conductor 116 and outer conductor 118 can each be composed of a conductive material (e.g., nitinol, copper, etc.). In some embodiments, the inner conductor 116 and outer conductor 118 are composed of the same conductive material, while in other embodiments the inner conductor 116 and outer conductor 118 can be composed of different conductive materials. The insulating layer 120 can be composed of a non-conductive material (e.g., a dielectric material such as a polymer). In some embodiments, the material of the insulating layer 120 may be chosen to provide a high axial stiffness along the axis A to allow greater rigidity to puncture tissue. Rigid materials such as PEEK or polyetherimide (such as those manufactured by SABIC of Riyadh, Saudi Arabia and sold under the trademark ULTEM) may be used, for example, to increase stiffness in the flexible instrument 100 and prevent buckling or kinking during a puncture operation.

The structures of the inner conductor 116, outer conductor 118, and/or insulating layer 120 can be configured to impart flexibility to the transmission member 102 and antenna body 112. For example, as shown in FIG. 1, the inner conductor 116 can be an elongated flexible structure (e.g., one or more wires, filaments, fibers, etc.) extending along the length of the transmission member 102 and antenna body 112. The insulating layer 120 can be a layer of solid material, or can include one or more filaments of non-conductive material that are braided, woven, or wrapped around the inner conductor 116. The outer conductor 118 can include one or more layers of material around the insulating layer 120. By varying construction of layers, flexibility of the elongate device and thus the flexible instrument 100 can be altered. For example, constructing the outer conductor 118 or insulating layer 120 of a solid tube or layers of concentric solid tubes, could provide for a stiffer flexible instrument 100 than use of a material wound in a ribbon layer or plurality of ribbon layers. A more flexible construction could be provided by constructing braided layers of filaments wound in different directions. Accordingly, in some embodiments, the outer conductor 118 includes at least one multi-filament layer having a plurality of filaments (e.g., ribbons, tapes, wires, fibers, etc.) that are braided or woven around the insulating layer 120. The filaments can be made of a conductive material (e.g., nitinol, copper, etc.). Alternatively or in combination, the outer conductor 118 can include at least one layer in which a single filament of conductive material is wrapped around the insulating layer 120 (e.g., a wrapped metal ribbon). Optionally, the outer conductor 118 can include at least one layer of a solid material (e.g., a foil layer, sheet, coating, a tube, etc.).

In some embodiments, the outer conductor 118 is composed entirely of a single material and/or structure. For example, the outer conductor 118 can include one or more filaments that are braided or wrapped along the entire length of the flexible instrument 100. As another example, the outer conductor 118 can include a thin solid tube that extends along the entire length of the flexible instrument 100. In other embodiments, however, different portions of the outer conductor 118 can be composed of different materials and/or structures. For example, the outer conductor 118 can include a combination of braided and wrapped materials, such as a first layer or region composed of a braided material, and a second layer or region composed of a wrapped material. As another example, the outer conductor 118 can include an outer braided multi-filament layer and an inner foil layer. In some examples, the foil layer could made of a material provided for shielding (e.g. copper). In other embodiments requiring higher stiffness, the inner layer can be made of a nitinol tube or ribbon providing for less conductivity than copper but higher stiffness and recoverability. In a further example, the outer conductor 118 can include a braided multi-filament layer, a foil layer, and a layer made of a resiliently flexible material (e.g., nitinol) to impart recoverability to the flexible instrument 100. In some embodiments, the material properties of the outer conductor 118 may vary down a length of the outer conductor 118. For example, a distal section may require higher stiffness to allow for puncturing of tissue by the flexible instrument 100. Accordingly, at a distal section the inner layer may be made of a nitinol tube and/or the outer layer may be made of a ribbon layer, while at a proximal section, the inner layer may be made of a foil layer and/or the outer layer may be braided.

The flexible instrument 100 can also include at least one jacket layer or coax jacket layer 122 (also referred to herein as an "intermediate layer") positioned over at least a portion of the outer conductor 118. In the illustrated embodiment, the jacket layer 122 extends along and surrounds the entire length of the outer conductor 118. Similarly, the jacket layer 122 can be formed over the entire length of the antenna body 112 and the transmission member 102. In other embodiments, however, the jacket layer 122 can be formed over only a portion of the outer conductor 118. For example, the jacket layer 122 can be located only at the distal section of the outer conductor 118, such as the region corresponding to the antenna body 112, and, optionally, a portion of the transmission member 102 (e.g., the distal portion 106). As another example, the jacket layer 122 can be localized to discrete regions of the outer conductor 118 at or near the locations where recesses are to be formed, as discussed further below.

The jacket layer 122 can improve the structural integrity of and/or provide mechanical support to at least a portion of the flexible instrument 100 (e.g., to the antenna body 112). Additionally, in embodiments where the outer conductor 118 is made of braided, woven, or wrapped filaments, the jacket layer 122 can hold the filaments together to reduce fraying or unraveling when the outer conductor 118 is cut to form a recess, as described in greater detail below. The jacket layer 122 can also be resiliently flexible to improve the recoverability of the flexible instrument 100 after deformation. Optionally, the jacket layer 122 can also increase the stiffness of the flexible instrument 100 along axis A, e.g., to facilitate puncturing of tissue. The jacket layer 122 can be sufficiently thin so the overall diameter of the flexible instrument 100 remains small enough to navigate narrow and/or tortuous passageways, while also avoiding interference with coolant flow around the flexible instrument 100 (described in greater detail below). For example, the thickness of the jacket layer 122 can be less than or equal to 30 microns, 25 microns, 20 microns, 15 microns, 10 microns, or 5 microns. In some embodiments, the thickness can be within a range from 25.4 microns to 6.35 microns. In some embodiments, the jacket layer 122 is composed of a non-conductive material, such as a polymer, a plastic, a PET coating, a heat-shrink material, or a combination thereof. In other embodiments, however, the jacket layer 122 may be composed of a partially conductive material (depending upon the positioning of the layer relative to the antenna body 112). The jacket layer 122 can be applied as a single layer of material, or can be applied in multiple layers by braiding multi-filament layers, wrapping ribbon layers, or heat shrinking.

In additional embodiments, one or more aspects of the inner conductor 116, outer conductor 118, insulating layer 120, and/or jacket layer 122 may be modified to help further prevent kinking while the flexible instrument 100 is bending through narrow and/or tortuous passageways. Such modifications can include, for example, varying layer thickness, material selection, and/or braiding to obtain an optimal stiffness for the flexible instrument 100 while simultaneously allowing for sufficient flexibility for navigation.

In some embodiments, the antenna body 112 is patterned with one or more recesses, such as a first recess 124a and a second recess 124b (collectively, "recesses 124"). The recesses 124 can be any structure configured to allow energy to radiate from the inner conductor 116, such as apertures, slots, grooves, channels, trenches, spirals, cuts, etc. As shown in FIG. 1, the recesses 124 are formed in and extend through the entire thickness of the jacket layer 122 and the outer conductor 118, with the insulating layer 120 and inner conductor 116 remaining intact. Alternatively, the recesses 124 can also be formed in and extend at least partially through the insulating layer 120, with the inner conductor 116 remaining intact. In embodiments where the recesses 124 extend through the entire thickness of the insulating layer 120, the exposed surfaces of the inner conductor 116 and/or outer conductor 118 at the recesses 124 can be sealed or otherwise insulated from each other (e.g., using a non-conductive material) to prevent electrical shorting between the inner conductor 116 and outer conductor 118 at those locations. The recesses 124 can be formed by cutting or otherwise removing portions of the jacket layer 122, outer conductor 118, and (in some instances) the insulating layer 120, as described in greater detail below.

The configuration of the recesses 124 (e.g., depth, number, position, size, shape, etc.) can form a recess pattern which can be selected to produce a desired pattern of energy radiation from the antenna body 112 and the proper frequency responses needed for the particular medium that the antenna body 112 is radiating in. The depth of the recess, the recess length, the spacing between the recesses 124, the number of recesses 124, the shape of the recesses 124, the positioning of the recesses 124 along antenna body 112, and/or the relative positioning of the recesses 124 to one another, can define the recess pattern. In the illustrated embodiment, for example, the first recess 124a is located at a distal tip portion 126 of the antenna body 112, and the second recess 124b is positioned proximal to the first recess 124a. The first recess 124a and second recess 124b can be separated from each other by a separation distance within a range from 3 mm to 10 mm, such as 6.5 mm. As shown in FIG. 1, the recesses 124 each extend partially or entirely around the circumference of the antenna body 112 to form a pair of arcuate or circular slots having rectangular cross-sectional shapes. The length of each recess 124 (e.g., as measured along the longitudinal direction parallel to axis A) can be greater than 0 mm and less than or equal to 10 mm (e.g., 1 mm). Optionally, the recesses 124 can have different dimensions, e.g., the first recess 124a can be longer than the second recess 124b, or vice-versa. In other embodiments, however, some or all of the recesses 124 can have the same dimensions, e.g., the first recess 124a can have the same length as the second recess 124b. The configuration of the recesses 124 shown in FIG. 1 can produce an energy radiation pattern having a spherical or generally spherical electric field profile, which may be beneficial for efficient tissue ablation. The configuration of the recesses 124 also affects the frequency response in a particular medium, which affects how efficiently the antenna body 112 radiates into the medium.

In other embodiments, for example, the antenna body 112 can include a different number of recesses 124 (e.g., one, three, four, or more). The locations of the recesses 124 can also be changed, e.g., the first recess 124a or the second recess 124b can be omitted, the antenna body can include one or more additional recesses between the first recess 124a and the second recess 124b, and so on. Additionally, one or more of the recesses 124 can have a different overall shape (e.g., linear, curved, curvilinear, annular, helical, serpentine, zig-zag, etc.) and/or cross-sectional shape (e.g., square, trapezoidal, triangular, circular, oval, etc.). Although FIG. 1 illustrates each recess 124 as extending circumferentially around the antenna body 112, in other embodiments one or more of the recesses 124 can be arranged differently, e.g., extending longitudinally along the length of the antenna body 112, extending helically around the antenna body 112, or any other suitable geometry.

In some embodiments, in addition to recesses 124, the outer conductor 118 may include patterning, e.g., a cut pattern within just the outer conductor 118 to alter flexibility. As compared to recesses 124, such patterning may not extend through the jacket layer 122 and would not alter delivery of energy. The patterning can include a number of different shapes/arrangements (e.g., discrete slits, spiral/helical slits or cuts, rectangular openings, H-shaped patterns, etc.). The patterning may extend along only a selected portion or portions of the outer conductor 118 along the length of the flexible instrument 100. Further, in some embodiments, the patterning can vary along the length of the outer conductor 118.

The antenna assembly 104 further includes one or more inserts coupled to the antenna body 112, such as a first insert 128a and a second insert 128b (collectively, "inserts 128"). Each insert 128 is positioned within a respective recess 124 to cover and protect the portions of the inner conductor 116 and/or insulating layer 120 at or near the recess 124. As previously described, when portions of the jacket layer 122, outer conductor 188, and/or insulating layer 120 are removed to form the recesses 124, the remaining portions of the insulating layer 120 and/or inner conductor 116 may lack sufficient mechanical strength and/or axial rigidity to withstand bending or other deformations that may occur during operation of the flexible instrument 100. Accordingly, the inserts 128 can reinforce the antenna body 112 at or near the recesses 124 to reduce the likelihood of mechanical failure (e.g., buckling, kinking) at those locations. The presence of the inserts 128 can also increase the stiffness of the antenna body 112 to facilitate puncturing of tissue.

The inserts 128 can be composed of a low RF or microwave loss non-conductive material to reduce interference with energy radiation from the inner conductor 116. The non-conductive material can be, for example, a plastic material (e.g., PTFE, PEEK, fluorinated ethylene propylene (FEP), polyurethane), a heat-shrink material, or a combination thereof. In some embodiments, the inserts 128 are provided as pre-formed solid components that are positioned within the recesses 124 and secured in place (e.g., using adhesives, fasteners, an additional layer of material over the inserts 128, etc.). For example, the inserts 128 can be tubes that are positioned within the recesses 124. The tubes can be slit or otherwise expandable to allow the tubes to slipped over the antenna body 112 and into the recesses 124. In other embodiments the inserts 128 can be composed of a filler (e.g., beads, fibers, glue, resin, foam, etc.) that are placed into the recesses 124, then solidified (e.g., by bonding, curing, adhering, etc.) to form the inserts 128. For example, the filler can be plastic beads (e.g., beads composed of regular PTFE, PTFE foam, FEP, PEEK, etc.). As another example, the filler can be a glue or other flowable material (e.g., polyurethane) that fills the recesses 124 and is subsequently hardened and/or cured in place to form the inserts 128. In some embodiments, the filler material is a low RF or microwave loss material that can also withstand the temperatures needed when the antenna body 112 is operating at or near maximum power.

In the illustrated embodiment, each insert 128 fills the entirety of the corresponding recess 124, with the geometry (e.g., size, shape) of each insert 128 being generally similar or identical to the geometry of the corresponding recess 124. For example, the inserts 128 can each be arcuate or annular structures (e.g., tubes, rings, bands, etc.) shaped to fit into the recesses 124. As shown in FIG. 1, the first insert 128a has a rectangular cross-sectional shape corresponding to the rectangular cross-sectional shape of the first recess 124a, and the second insert 128b has a rectangular cross-sectional shape corresponding to the rectangular cross-sectional shape of the second recess 124b. Likewise, the length and height of each insert 128 can match the length and height of the respective recess 124. In other embodiments, however, the inserts 128 may not fill the entire recess 124. For example, the inserts 128 can fill only the portions of the recess 124 closest to the inner conductor 116, while leaving the other portions of the recess 124 empty. In such embodiments, the geometry of the inserts 128 can be different from the geometry of the corresponding recesses 124 (e.g., the inserts 128 can have a smaller length and/or height compared to the recesses 124).

In some embodiments, the antenna assembly 104 further includes a cap structure 114 coupled to the distal tip portion 126 of the antenna body 112, e.g., at a location distal to the first recess 124a and first insert 128a. The cap structure 114 can be coupled to the inner conductor 116 (e.g., by soldering), formed on the inner conductor 116, or integrally formed with the inner conductor 116. The cap structure 114 can be made of a conductive material, such as a metal (e.g., nitinol, copper, etc.). For example, the cap structure 114 may be formed from a conductive metal tube (e.g., nitinol, copper, etc.) surrounding a portion of the inner conductor 116 extending distally beyond the outer conductor 118 and distal tip portion 126 of the antenna body 112. The cap structure 114 can be electrically coupled with solder to the inner conductor 114. The geometry of the cap structure 114 (e.g., shape, length, diameter, etc.) can be configured to affect the energy radiation pattern of the antenna assembly 104. For example, in the illustrated embodiment, the cap structure 114 has a generally cylindrical shape with a length within a range from 1 mm to 3 mm (e.g., 2 mm), and a diameter identical or similar to the combined diameter of the inner conductor 116, outer conductor 118, and insulating layer 120. In other embodiments, however, the cap structure 114 can have a different shape, such as a conical, pointed, domed, hemispherical, or rounded shape. For example, the cap structure 114 can have a conical or pointed shape, e.g., to allow the flexible instrument 100 to puncture tissue. In still other embodiments, the cap structure 114 may be optional and may be omitted from the antenna assembly 104. In such embodiments, a portion of the inner conductor 116 can extend distally beyond the outer conductor 118 and the distal tip portion 126 of the antenna body 112.

Optionally, at least a portion of the cap structure 114 (e.g., the distal end of the cap structure 114) can be sealed with a plug (not shown). The plug can be made of a non-conductive material, such as glue or another adhesive, a conformal coating (e.g., a parylene coating or vapor-deposited coating), or a reflowable material. In some embodiments, for example, the plug is formed by adding glue to the distal end of the cap structure 114. As another example, the plug can be formed by molding a reflowable material with a glass mold. The plug can be configured to seal the cap structure 114 and/or other portions of the antenna assembly 104 from ingress of fluid.

The recess pattern and the length, diameter, and/or shape of the cap structure 114 (if the antenna assembly 104 includes the cap structure 114), all affect the frequency behavior and the resulting radiation into the medium. The configuration of the recesses 124 and inserts 128 can also be varied as desired to produce different energy radiation patterns.

The flexible instrument 100 can include one or more additional layers of material over the antenna assembly 104. As shown in FIG. 1, for example, the flexible instrument 100 includes a barrier layer 130 positioned over at least a portion of the antenna assembly 104 (e.g., the outer conductor 118, jacket layer 122, inserts 128, and/or cap structure 114). In embodiments where the cap structure 114 is sealed with a plug, the barrier layer 130 can extend partially or entirely over the cap structure 114 and plug. In some embodiments, the barrier layer 130 is localized only to the portions of the antenna assembly 104 at or near the locations of the recesses 124 and inserts 128. In other embodiments, however, the barrier layer 130 can extend over the entire length of the antenna assembly 104. Optionally, the barrier layer 130 can also extend partially or completely over the transmission member 102.

The barrier layer 130 can create a barrier or seal to prevent inward migration of fluid (e.g., coolant, body fluid, etc.). For example, the barrier layer 130 can prevent fluid from moving beyond the inserts 128 and toward the inner conductor 116 and/or insulating layer 120. The barrier layer 130 can also seal the distal tip 110 of the antenna assembly 104 to prevent entry of fluid. In some embodiments, the barrier layer 130 also secures the inserts 128 within the recesses 124, in addition or as an alternative to adhesives. Optionally, the barrier layer 130 can provide mechanical stability and axial rigidity to the flexible instrument 100. In some embodiments, the barrier layer 130 can include multiple layers, e.g., an inner barrier layer (not shown) which can help secure the inserts 128 and the cap structure 114 and/or an outer barrier layer (not shown) which can provide the seal to prevent fluid ingress. In some embodiments, multiple layers may be used to achieve desired bending and stiffness, by using various materials and varying the number of layers.

The barrier layer 130 may be formed of a flexible and fluid impermeable material. In some embodiments, the barrier layer 130 is composed of a non-conductive material, such as a polymer (e.g., fluropolymer), a plastic, a PET coating, a heat-shrink material, or other conformal coating (e.g., a parylene coating or vapor-deposited coating), or a combination thereof. The barrier layer 130 may be thin and form fit around the components of the flexible instrument 100, or may maintain a flexible tubular form. Optionally, the region of the barrier layer 130 at the distal tip 110 of the antenna assembly 104 can be formed from or sealed with an adhesive. In such embodiments the adhesive may be composed of the same material as the rest of the barrier layer 130, or may be composed of a different material.

Although FIG. 1 illustrates a particular configuration for the flexible instrument 100, it will be appreciated that this configuration can be varied in many different ways. For example, other elongate device configurations with different configurations, shapes, etc. of the inner conductor 116, outer conductor 118, and insulating layer 120 can be used. As another example, the flexible instrument 100 can include additional layers of material (e.g., insulating layers, jacket layers, barrier layers, etc.) not shown in FIG. 1. Additionally, although FIG. 1 depicts the transmission member 102 and antenna assembly 104 as being integrally formed with each other, in other embodiments the transmission member 102 and antenna assembly 104 can be discrete components that are subsequently coupled to each other. For example, the transmission member 102 can be formed from a first elongate device section and the antenna assembly 104 can be formed from a second, different elongate device section that is distinct from the first elongate device section. The second elongate device section can be fixedly coupled to the distal end of the first elongate device section to form the flexible instrument 100. In such embodiments, the first and second elongate device sections can each have a respective inner conductor, outer conductor, and insulating layer with features that are identical or generally similar to the features of the inner conductor 116, outer conductor 118, and insulating layer 120.

FIG. 2 is a side cross-sectional view of a flexible instrument 200 for tissue ablation configured in accordance with another embodiment of the present technology. The flexible instrument 200 is generally similar to the flexible instrument 100 of FIG. 1 such that like reference numerals are used to identify like elements illustrated in FIGS. 1 and 2 (e.g., transmission member 102 versus transmission member 202). Accordingly, the discussion of the flexible instrument 200 will be limited to those features that differ from the flexible instrument 100 of FIG. 1.

The flexible instrument 200 includes an antenna assembly 204 having an antenna body 212 with a first recess 224a and a second recess 224b. In contrast to the flexible instrument 100 of FIG. 1, the first recess 224a is not located at the distal tip portion 226 of the antenna body 212. Instead, the first recess 224a is proximal to and spaced apart from the distal tip portion 226, such that the outer conductor 218 and jacket layer 222 at the distal tip portion 226 remain intact. The distance between the first recess 224a and the distal tip portion 226 can be greater than 0 mm and less than or equal to 10 mm.

Additionally, rather than a cap structure, the antenna assembly 202 includes a conductive material 250 coupled to the distal tip portion 226 of the antenna body 212. In one embodiment, the conductive material 250 can be electrically coupled to the inner conductor 218 only or the outer conductor 216 only. In another embodiment, however, the conductive material 250 can electrically couple (e.g., electrically short) the inner conductor 216 with the outer conductor 218 of the antenna body 212. The conductive material 250 may comprise solder or other suitable conductive materials. The conductive material 250 may also comprise copper (e.g., a copper tube). The geometry (e.g., shape, length, diameter, etc.) of the conductive material 250 can be configured to affect the energy radiation pattern of the antenna assembly 104. Optionally, at least a portion of the conductive material 250 (e.g., the distal end of the conductive material 250) can be sealed with a plug (not shown). The plug can be made of a non-conductive material, such as glue or another adhesive, a conformal coating (e.g., a parylene coating or vapor-deposited coating), or a reflowable material. In some embodiments, for example, the plug is formed by adding glue to the distal end of the conductive material 250, or by molding a reflowable material with a glass mold. The plug can be configured to seal the conductive material 250 and/or other portions of the antenna assembly 204 from ingress of fluid.

Figures 3, 4:
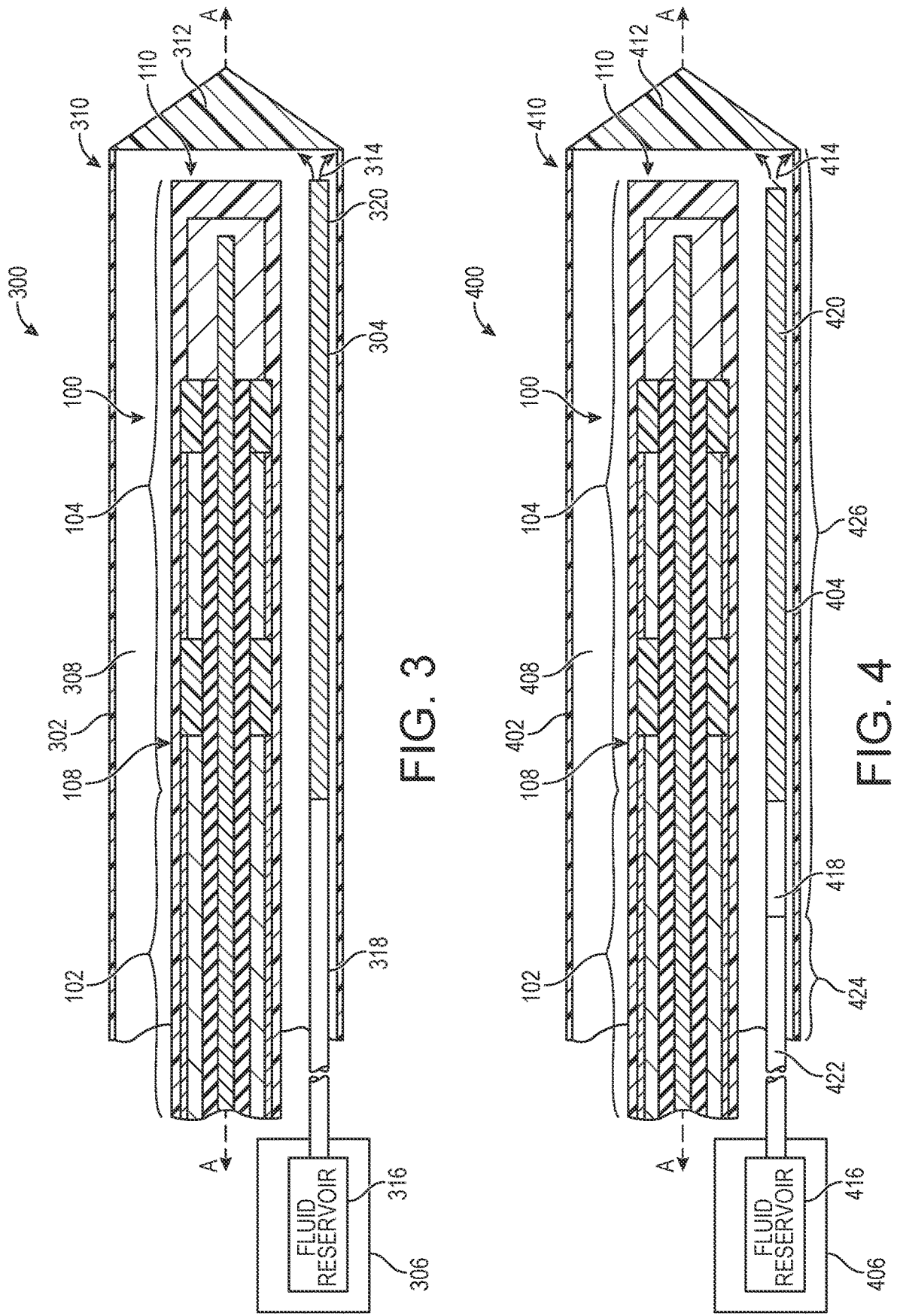
FIG. 3 is a side cross-sectional view of an energy delivery system for tissue ablation configured in accordance with an embodiment of the present technology.
FIG. 4 is a side cross-sectional view of an energy delivery system for tissue ablation configured in accordance with another embodiment of the present technology.

FIG. 3 is a side cross-sectional view of an energy delivery system 300 for tissue ablation configured in accordance with an embodiment of the present technology. In the illustrated embodiment, the energy delivery system 300 includes the flexible instrument 100 of FIG. 1, a sheath 302, at least one fluid conduit 304, and a fluid cooling system 306. In other embodiments, however, the flexible instrument 100 can be replaced with any of the other embodiments of flexible instruments described herein (e.g., flexible instrument 200 of FIG. 2).

The sheath 302 is an elongated hollow structure having a central lumen or channel 308 extending between a distal end portion 310 and a proximal end portion (not shown). The flexible instrument 100 is disposed within the central lumen 308. In some embodiments, the sheath 302 may be formed from a thermoplastic material or from other flexible and fluid impermeable materials. In some embodiments, the sheath 302 is closed, sealed, or otherwise restricts fluid from passing into or out of the sheath 302. For example, the sheath 302 can be coupled to and/or sealed by a tip section 312 at the distal end portion 310 of the sheath 302. The tip section 312 may allow the sheath 302 to more easily puncture anatomic tissue. In some embodiments, the tip section 312 may be formed in any shape, including any number of faces forming the tip, at any angle, and/or with any ratio of sizes (e.g., width vs. length) that will optimize tissue penetration. In the illustrated embodiment, for example, the tip section 312 is a conical structure with a triangular cross-sectional shape. In other embodiments, the tip section 312 can have a different shape, such as a domed, hemispherical, or rounded shape. The tip section 312 can be formed using glass molds or other suitable techniques. The tip section 312 may be composed of fluoropolymers, e.g., ethylene tetrafluoroethylene (ETFE), PEEK, other high temperature plastic materials, and/or other suitable materials. In still further embodiments, the tip section 312 may have other configurations/features. For example, one or more portions of the tip section 312 may be radiopaque. In such embodiments, the tip section 312 may comprise a material or materials to make the tip section radiopaque and/or the tip section may include an insert made of a highly radiopaque material.

Various tips for optimizing tissue penetration are described in U.S. patent application Ser. No. 16/670,846 filed Oct. 31, 2019, disclosing "Tissue Penetrating Device Tips" and PCT App No. PCT/US19/24564 filed Mar. 28, 2019, disclosing "Systems and Methods Related to Flexible Antennas," which are both incorporated by reference herein in their entireties. Alternatively or in combination, the sheath 302 may have openings, slits, or otherwise be unsealed at or along any portion of the sheath 302 (e.g., at the distal end portion 310 of the sheath 302) to allow fluid to pass into the sheath 302 or out from the sheath 302. Optionally, the tip section 312 can be omitted, and the distal end portion 310 can have a flat end face, or can be left open.

The fluid cooling system 306 can be configured to cool the flexible instrument 100 by introducing a coolant (e.g., a fluid 314 or another liquid or gaseous cooling agent) into the central lumen 308 (e.g., also referred to herein as a chamber or channel) of the sheath 302. The fluid 314 may be, for example, water or a saline solution. The fluid cooling system

306 can be coupled to the central lumen 308 and/or the sheath 302 to deliver the fluid 314 into the central lumen 308. The fluid cooling system 306 may include a fluid reservoir 316 (shown schematically) and other components such as pumps, valves, refrigeration systems, suction systems, and/or sensors (not shown). In the illustrated embodiment, for example, the fluid cooling system 306 includes or is coupled to at least one fluid conduit 304 that extends through at least a portion of the central lumen 308 within the sheath 302. The fluid conduit 304 can extend along at least a portion of the flexible instrument 100, such as along the transmission member 102 and/or the antenna assembly 104. The fluid 314 may be directed within the central lumen 308 through the fluid conduit 304. Accordingly, a channel may be formed between the flexible instrument 100 and the interior of the sheath 302. In some embodiments, the fluid conduit 304 may extend to at least a distal end portion of the antenna assembly 104 to provide recoverable flexibility and support along a maximized length of the flexible instrument 100 and an added benefit of delivering coolant to the distal end portion of the antenna assembly 104 for increased and/or more uniform cooling of the antenna. Further details regarding such embodiments are described below with reference to FIGS. 9A-16.

The flexible instrument 100 can have an outer diameter that is sufficiently small to reduce or avoid interference with flow of the fluid 314 through the channel. For example, the outer diameter of the flexible instrument 100 can be less than or equal to 2 mm, 1.75 mm, 1.5 mm, 1.25 mm, 1 mm, or 0.75 mm. In some embodiments, the maximum clearance between the outer surface of the flexible instrument 100 and the inner surface of the sheath 302 can be at least 0.1 mm, 0.25 mm, 0.5 mm, 0.75 m, 1 mm, or 1.25 mm.

The fluid cooling system 306 may be an open loop system, a partially open loop system, a closed loop system, or any other suitable type of cooling system. The fluid conduit 304 may be used, for example, to provide inflow of the fluid 314 to the central lumen 308. The fluid 314 can circulate about the antenna assembly 104 and/or the transmission member 102 within the central lumen 308, and can return in a proximal direction within the central lumen 308 to be purged in a reservoir (not shown) or purged to the environment. In other embodiments, the fluid 314 can exit the sheath 302 via openings or slits in the sheath 302, or return to the fluid cooling system 306 via the central lumen 308 and/or another fluid conduit (not shown). Alternatively, the fluid conduit 304 can be used to provide return flow of the fluid 314 from the central lumen 308 by discontinuing inlet fluid from the fluid reservoir 316, reversing flow, and providing suction to the fluid conduit 304 using the fluid cooling system 306. In other embodiments, a separate fluid conduit (not shown) can be provided that does not provide inflow of fluid 314 and is only used for return flow. In some embodiments, the return flow can be purged in a combination of flow through the central lumen 308 in a proximal direction, flow through fluid conduits, and/or through openings in sheath 302.

During operation of the energy delivery system 300, the sheath 302 containing the flexible instrument 100 is inserted into the patient's anatomy and navigated to a target site. To facilitate delivery of the sheath 302 and flexible instrument 100 to the target site, the sheath 302 and/or flexible instrument 100 must be sufficiently flexible to navigate tortuous anatomical passageways. In addition, the distal section of the sheath 302 and/or flexible instrument 100 typically undergoes substantial deformation during delivery to the target site. Thus, the sheath 302 and/or flexible instrument 100 must be able to recover to an initial (e.g., undeformed) shape or state after deformation to reduce trajectory error once near a target site, where puncturing of tissue is required to accurately deliver the antenna assembly 104 to the target site. Accordingly, in some embodiments, the sheath 302 itself is composed of one or more materials that provide mechanical properties for recoverability (e.g., spring back) and stiffness. For example, the sheath 302 can be formed of a resiliently flexible material (e.g., nitinol or another suitable shape memory material). The sheath 302 may be composed a non-conductive material and/or a conductive material (e.g., depending upon positioning relative to the antenna assembly). Alternatively or in combination, the flexible instrument 100 may include resiliently flexible materials, as previously described. Additionally, in some embodiments, the fluid conduit 304 is also composed partially or entirely of a resilient flexible material to provide recoverability. However, many shape memory and other resiliently flexible materials (including nitinol) are conductive at the microwave frequency range (e.g., 300 MHz to 300 GHz), meaning that any region of the fluid conduit 304 that runs alongside the antenna assembly 104 within the sheath 302 and is formed of a conductive material would interfere with the antenna assembly 104 during energy delivery.

Accordingly, the fluid conduit 304 can include a first region 318 formed of a resiliently flexible material (e.g., a shape memory material such as nitinol) and a second region 320 formed of a non-conductive material (e.g., PEEK, PTFE, PET, or another suitable plastic or polymer material). The first region 318 extends along the transmission member 102 and the second region 320 extends along the antenna assembly 104. As illustrated in FIG. 3, the first region 318 terminates at a point along the length of the flexible instrument 100 proximate to the proximal portion 108 of the antenna assembly 104 such that the first region 318 does not interfere with the antenna assembly 104 during energy delivery. The second region 320 can terminate at or near the distal tip 110 of the antenna assembly 104, or can extend to the distal end portion 310 of the sheath 302 (e.g., to provide stiffness and axial rigidity along the entire length of the flexible instrument 100 and/or sheath 302). Because the second region 320 of the fluid conduit 304 is formed of a material that is non-conductive at the frequency range of the antenna assembly 104, the second region 320 does not interfere with the antenna assembly 104 during energy delivery.

In this manner, the fluid conduit 304 illustrated in FIG. 3 provides the flexibility to navigate the sheath 302 and flexible instrument 100 throughout patient anatomy as well as the rigidity to accurately deliver the antenna assembly 104 to a target site during a puncture operation. In particular, the first region 318 of the fluid conduit 304 provides recoverable flexibility to the sheath 302 while the second region 320 of the fluid conduit 304 provides added stiffness to the portion of the sheath 302 corresponding to the antenna assembly 104 without interfering with the antenna assembly 104 during energy delivery. In addition, the first and second regions 318 and 320 of the fluid conduit 304 provide axial rigidity along the axis A to facilitate delivery of the antenna assembly 104 to a target site during a puncture operation while reducing the likelihood of buckling or kinking along the sheath 302 and/or flexible instrument 100.

It will be appreciated that, in some instances, a transition section between the first and second regions 318 and 320 may be a point of weakness along the length of the flexible instrument 100, and in some instances can cause kinking. To help address this issue, the second region 320 of the fluid conduit 304 can be joined to the first region 318 using any of a variety of methods to help provide a consistent and reliable connection. For example, in some embodiments to form the fluid conduit 304, a tube forming the second region 320 (e.g., a tube composed of PEEK or plastic material) can be inserted into a tube forming the first region 318 (e.g., a tube composed of nitinol), and then the mating ends of the two tubes can be tapered. In another embodiment, the proximal end portion of the second region 320 can be spliced to extend over or within the distal end portion of the first region 318. As another example, the second region 320 can be butt-jointed and welded or glued with the first region 318. As still another example, the first region 318 can be slot cut to reduce its stiffness (e.g., as described in greater detail below with respect to FIG. 5) and then overlapped with the second region 320 to create a gradual transition between the first and second regions 318 and 320. In some embodiments, a FEP layer may surround the fluid conduit 304 to aid in joining the first region 318 and the second region 320. In some embodiments, a transition section between the first region 318 (e.g., composed of nitinol) and the second region 320 (e.g., composed of plastic or polymer material) may be composed of a mixture of the two different materials. In other embodiments, however, the transition section may have a different composition.

Although FIG. 3 illustrates a single fluid conduit 304, in other embodiments the energy delivery system 300 can include multiple fluid conduits 304 (e.g., two, three, or more). In such embodiments, each fluid conduit 304 can be separate from one another such that each can flex independently of one another when the sheath 302 is navigated to a target. In some embodiments, separate fluid conduits 304 provide greater recoverable flexibility and/or axial rigidity than fluid conduits 304 that are attached to one another. In other embodiments of the present technology, however, the fluid conduits 304 can be joined to one another and/or can be formed as a single structure. Each fluid conduit 304 can be fixed within the sheath 302, or can be slidable or otherwise movable within the sheath 302 (e.g., distally and/or proximally along a direction parallel with the axis A). In still further embodiments including multiple fluid conduits 304, the conduits 304 can be staggered longitudinally (i.e., the longitudinal positioning of the distal ends of the tubes can be different along the length of the device.) Additionally, in embodiments including multiple conduits 304, the portions of the individual conduits 304 that composed of different materials (i.e., the first regions and the second regions) can differ between the different conduits 304. For example, the longitudinal lengths of the first regions 318 (e.g., composed of nitinol) relative to the lengths of the second regions 320 (e.g., composed of plastic material(s)) can vary between the individual conduits. Moreover, in some embodiments, the slot cut patterns for the individual conduits 304 can also vary.

FIG. 4 is a cross-sectional view of an energy delivery system 400 configured in accordance with another embodiment of the present technology. The energy delivery system 400 is generally similar to the energy delivery system 300 of FIG. 3 except that the fluid conduit 404 of the energy delivery system 400 illustrated in FIG. 4 includes a third region 422 proximal to the first region 418. Accordingly, like reference numerals are used to identify like elements illustrated in FIGS. 3 and 4, and the discussion of the energy delivery system 400 will be limited to those features that differ from the energy delivery system 300 of FIG. 3. Further, it will be appreciated that the components of the energy delivery system 400 may have many of the same features and advantages as the energy delivery system 300 described above.

As illustrated in FIG. 4, the sheath 402 includes a proximal section 424 and a distal section 426. The distal section 426 extends distally from the proximal section 424 at a point along the length of the transmission member 102 to at least the distal tip 110 of the antenna assembly 104 (e.g., to the distal end 410 of the sheath 402). The third region 422 of the fluid conduit 404 can extend along at least a portion of the proximal section 424 of the sheath 402, while the first region 418 of the fluid conduit 404 can extend along at least a portion of the distal section 426 of the sheath 402 to provide recoverable flexibility along this portion of the sheath 402. The second region 420 of the fluid conduit 404 can extend along the antenna assembly 104, terminating at or near the distal tip 110 of the antenna assembly 104.

Resiliently flexible materials, such as nitinol or other shape memory materials, are often expensive relative to other materials. Moreover, the proximal section 424 of the sheath 402 typically does not undergo the extent of deformation experienced by the distal section 426 of the sheath 402. As such, recoverable flexibility can be less of a concern along the proximal section 424 of the sheath 402 than the distal section 426. Therefore, to reduce costs, the third region 422 of the fluid conduit 404 can be formed of a material that is less expensive than the resiliently flexible material (e.g., nitinol) used to form the first region 418 of the fluid conduit 404. For example, the third region 422 of the fluid conduit 404 can be formed of a plastic, a polymer, or other suitable material (e.g., stainless steel) which can provide support and axial rigidity to the proximal section 424 of the sheath 402 but does not provide the recoverable flexibility offered by a more expensive material such as nitinol. In some embodiments, the material used to form the third region 422 of the fluid conduit 404 can be selected based on a desired flexibility (e.g., stiffness) and/or axial rigidity of the proximal section 424 of the sheath 402. The second region 420 can be formed of a non-conductive material as previously described. In alternative embodiments where cooling and rigidity needs do not require the fluid conduit 404 to extend to the distal tip 110 of antenna assembly 104, the second region 420 can be omitted.

The third region 422 of the fluid conduit 404 can be joined to the first region 418 using any of a variety of methods. For example, the distal end portion of the third region 422 can be spliced to extend over or within the proximal end of the first region 418. Alternatively, the distal end portion of the third region 422 can be shrunk and at least partially overlapped by the proximal end of the first region 418. As another example, the third region 422 can be butt-jointed with or glued or welded to the first region 418. As still another example, the first region 418 can be slot cut to reduce its stiffness (e.g., as described in greater detail below with respect to FIG. 5) and then be overlapped with the third region 422 to create a gradual transition between the regions 422 and 418. In some embodiments, a FEP layer may surround the fluid conduit 404 to aid in joining the third region 422 and the first region 418.

Figures 5, 6A, 6B:
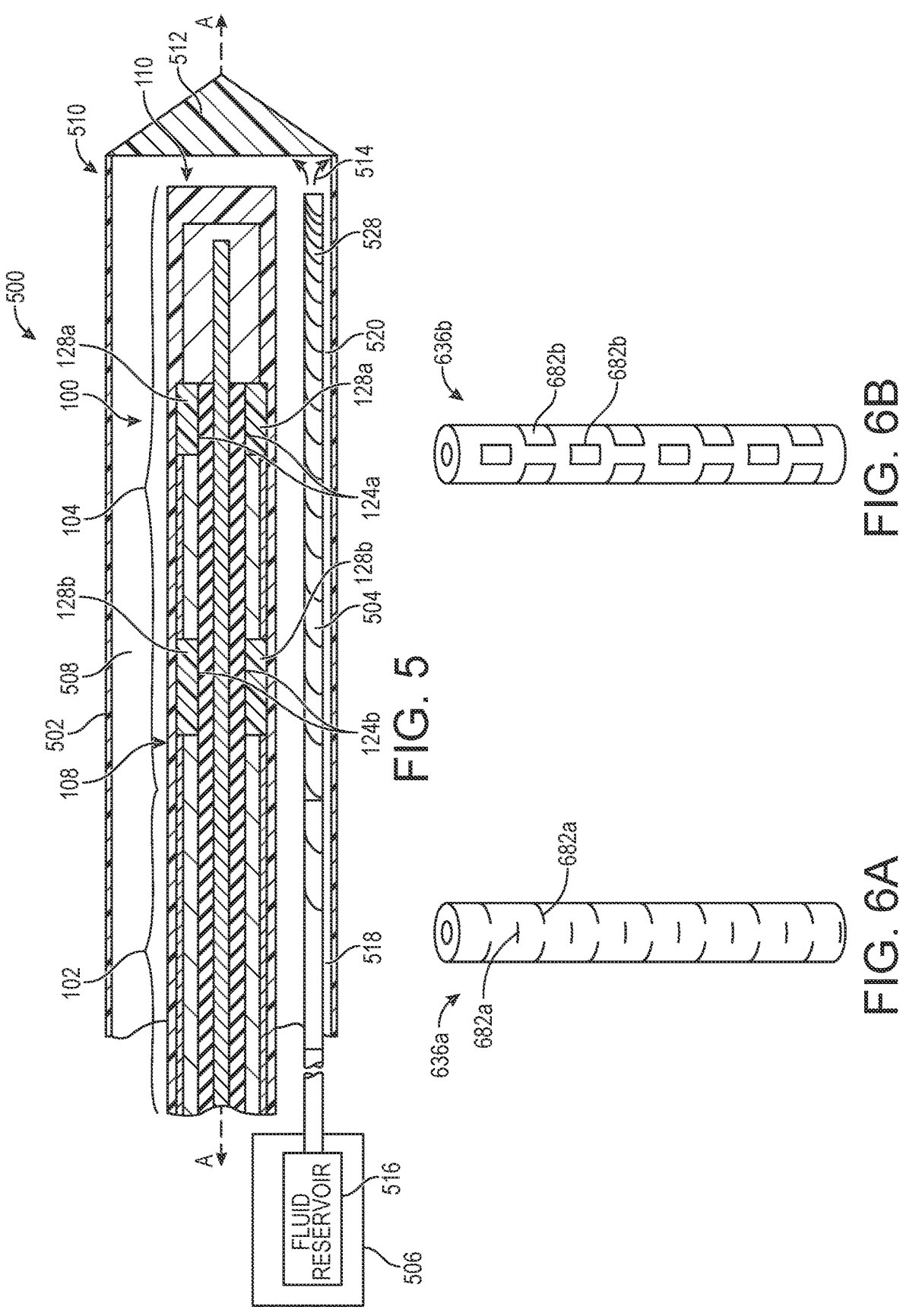
FIG. 5 is a side cross-sectional view of an energy delivery system for tissue ablation configured in accordance with a further embodiment of the present technology.
FIGS. 6A and 6B are side views of patterned fluid conduits configured in accordance with various embodiments of the present technology.

FIG. 5 is a cross-sectional view of an energy delivery system 500 configured in accordance with a further embodiment of the present technology. The energy delivery system 500 is generally similar to the energy delivery systems 300/400 of FIGS. 3 and 4 except that the fluid conduit 504 illustrated in FIG. 5 is patterned with a plurality of slots 528 (e.g., cutouts, slits, etc.). Accordingly, like reference numerals are used to identify like elements illustrated in FIGS. 3-5, and the discussion of the energy delivery system 500 will be limited to those features that differ from the energy delivery systems 300/400 of FIGS. 3 and 4. Further, the components of the energy delivery system 500 may have many of the same features and advantages as the energy delivery systems 300 and 400 described above.

As shown in FIG. 5, the fluid conduit 504 includes a first region 518 and a second region 520. In the illustrated embodiment, both the first region 518 and the second region 520 of the fluid conduit 504 include a gradient of slots 528 along their lengths to vary the stiffness of the corresponding regions 518 and 520 of the fluid conduit 504. For example, the fluid conduit 504 can include slots 528 at various locations along the first region 518 and/or the second region 520 to vary the stiffness of the fluid conduit 504 such that the transition between the first region 518 and the second region 520 is gradual (e.g., to maintain structural integrity of the fluid conduit 504 across the transition portion). As another example, the first region 518 and/or the second region 520 of the fluid conduit 504 can include a greater number of slots 528 at locations where a greater amount of flexibility is desired and/or a lesser number of slots 528 at locations where a greater amount of stiffness is desired. As shown in FIG. 5, for example, both the first region 518 and the second region 520 include spiral slots or slits 528 along their lengths. The second region 520 includes a greater number of spiral slots 528 toward the distal tip 110 of the antenna 104 to increase the flexibility of the fluid conduit 504 along this portion of the fluid conduit 504. The number of spiral slots 528 decreases proximally over the length of the second region 520 and over the transition from the second region 520 to the first region 518 such that the fluid conduit 504 maintains a greater amount of stiffness and/or recoverable flexibility along this portion of the fluid conduit 504 and/or such that the transition between the first region 518 and the second region 520 is gradual.

Although the fluid conduit 504 is illustrated as having spiral slots 528, fluid conduits configured in accordance with other embodiments of the present technology can include slots of other shapes and/or patterns. For example, FIG. 6A is a side view of a patterned fluid conduit 604a having a plurality of slots 628a in the shape of discrete slits. As another example, FIG. 6B is a side view of a patterned fluid conduit 604b having a plurality of slots 628b in the shape of rectangular cutouts. Both the slots 628a (FIG. 6A) and the slots 628b (FIG. 6B) are cut into the fluid conduits 604a and 604b, respectively, in an "H" pattern. Other patterns (e.g., spiral, zig zag, straight, etc.) are of course possible and within the scope of the present technology.

Referring again to FIG. 5, in some embodiments, the patterning of the slots 528 can be configured to reinforce point of weakness along the flexible instrument 100 and/or sheath 502. For example, the portions of the flexible instrument 100 containing the recesses 124 and inserts 128 can be relatively weak compared to the remaining portions of the flexible instrument 100. Accordingly, the fluid conduit 504 can include fewer or no slots 528 near those portions of the flexible instrument 100. Additionally, patterned slots can be utilized to create a more gradual transition between components made from different materials to reduce or eliminate weaknesses associated with these points.

In some embodiments, one or more of the slots 528 in can serve as points of exit for the fluid 514 to exit the fluid conduit 504 and enter the central lumen 508 (or vice versa). For example, fluid 514 can be delivered to the central lumen 508 during delivery of the sheath 502 and flexible instrument 100 to a target site within a patient. In these embodiments, the fluid 514 can exit one or more of the slots 528 and fill the central lumen 508, thereby increasing stiffness of the sheath 502 and/or flexible instrument 100 during navigation of patient anatomy and to reduce the likelihood that the sheath 502 and/or flexible instrument 100 will buckle or kink during a puncture operation. Additionally, or alternatively, heat-shrink (not shown) can be laminated on the outside of all or a portion of the first region 518 and/or all or a portion of the second region 520 to prevent the fluid 514 from entering or exiting one or more of the slots 528 in the fluid conduit 504.

Although the energy delivery systems 300-500 described with respect to FIGS. 3-6B are fluid-cooled systems, in other embodiments the energy delivery systems described herein can be cooled using other techniques, or can be non-cooled systems. For example, a non-cooled energy delivery system can include a flexible instrument (e.g., flexible instrument 100 of FIG. 1 or flexible instrument 200 of FIG. 2) inserted into a sheath (e.g., sheath 302 of FIG. 3, sheath 402 of FIG. 4, or sheath 502 of FIG. 5) without any fluid conduits or other cooling components. Optionally, a non-cooled energy delivery system can include a flexible instrument (e.g., flexible instrument 100 of FIG. 1 or flexible instrument 200 of FIG. 2) by itself without any sheath.

FIG. 7 is a flow diagram illustrating a method 700 for manufacturing an energy delivery system in accordance with an embodiment of the present technology. The method 700 is illustrated as a set of steps, operations, or processes 710-780, and is described with additional reference to FIG. 1. Beginning at step 710, the method 700 includes applying a jacket layer (e.g., jacket layer 122) over at least a portion of an elongate device for transmission of energy (e.g., a coaxial cable). The elongate device can include an inner conductor (e.g., inner conductor 116), an insulating layer (e.g., insulating layer 120), and an outer conductor (e.g., outer conductor 118) surrounding the inner conductor. As previously described, the jacket layer can be formed from various materials such as plastic, PET coating, or heat-shrink. The jacket layer can be applied as a single layer of material, or can be applied in multiple layers by braiding multi-filament layers, wrapping ribbon layers, or heat shrinking. Additionally, as discussed above, the jacket layer can be sufficiently thin (e.g., less than or equal to 25 microns) so that the overall diameter of the elongate device remains small enough to navigate narrow and/or tortuous passageways, while also avoiding interference with coolant flow around the device. In embodiments where the elongate device is a coaxial cable including a thick material layer (e.g., greater than 25 microns) over the outer conductor, step 710 can include removing the thick material layer before applying the thin jacket layer.

In some embodiments, the jacket layer is formed over the entire length of the outer conductor. In other embodiments, however, the jacket layer can be formed over only a portion of the outer conductor. For example, the jacket layer can be located only at the distal region of the outer conductor. As another example, the jacket layer can be localized to discrete regions of the outer conductor at or near the locations where recesses are to be formed.

At step 720, the method 700 includes forming one or more recesses (e.g., recess 124a, 124b) in the elongate device (e.g., coaxial cable) to form an antenna body (e.g., antenna body 112). The recess(es) can be formed, for example, by cutting or otherwise removing a portion of outer conductor covered by the jacket layer, and the corresponding portion of a jacket layer over the portion of the outer conductor. The jacket layer can prevent layers of braided, wrapped, or foiled material from fraying or unraveling during cutting. In some embodiments, various layers of the outer conductor can be additionally peeled away to expose the insulating layer. Optionally, a corresponding portion of an insulating layer near the portion of the outer conductor can be removed. The recess(es) can be formed using cutting tools (e.g., a blade), lasers, or any other suitable technique. Optionally, step 720 can include forming multiple recesses in the antenna body (e.g., two, three, four, or more recesses). The number, position, and geometry of the recess(es) can be configured to produce a desired energy radiation pattern, as previously described.

At step 730, an insert (e.g., insert 128) is positioned within each recess. In some embodiments, the insert is a pre-formed component (e.g., a slit tube) that is shaped to fit within the recess. For example, a tube can be slipped over the antenna body and placed into the recess. In such embodiments, the insert can be secured within the recess by adhesives and/or by positioning a layer of material (e.g., barrier layer 130) over the insert. In other embodiments, the insert can be formed from filler materials (e.g., plastic beads, glue, flowable material) that are introduced into the recess and subsequently fixed in place (e.g., by curing, hardening, gluing, bonding, etc.). In embodiments where the antenna body include multiple recesses, an insert can be positioned within each recess.

At optional step 740, a conductive material (e.g., cap structure 114 or conductive material 250 (FIG. 2)) can be coupled or formed on a distal tip portion (e.g., distal tip portion 126) of the antenna body by soldering or other suitable techniques. The conductive material can be coupled to or formed on the inner conductor of the antenna body at the distal tip portion. For example, when cutting a recess at a distal tip portion of the elongate device (e.g. the recess 124a at distal tip portion 126), a portion of the inner conductor can be exposed to extend distally past the distal tip portion. The conductive material formed of a tube can placed around and soldered to the exposed inner conductor or formed and welded around to the inner conductor. Optionally, the conductive material can also be coupled to or formed on the outer conductor of the antenna body at the distal tip portion to electrically couple (e.g., electrically short) the inner conductor with the outer conductor. The conductive material can have a geometry configured to affect the energy radiation pattern produced by the antenna body, as previously described.

At step 750, a barrier layer (e.g., barrier layer 130) can be positioned over an antenna assembly (e.g., antenna assembly 104) that encompasses the antenna body, the insert, and the conductive material. The barrier layer can secure the insert within the recess and secure the conductive material to the inner conductor and the antenna body. The barrier layer can additionally be positioned over at least the insert and recess to prevent fluid migration into the antenna body. In some embodiments, the barrier layer also extends over the distal tip of the antenna assembly to prevent inward migration of fluid via the distal tip. Optionally, the barrier layer can extend over the entire length of the antenna assembly. The barrier layer can also extend over other portions of the energy delivery system, such as over a portion of a transmission member (e.g., transmission member 102) or over the entire length of the transmission member. The barrier layer can be applied as heat shrink tubing, heated and melted over the antenna assembly/transmission member or applied as a coating (e.g., parylene coating or vapor-deposited coating). In some embodiments the barrier layer may be applied in multiple layers including a first layer to secure the inserts and the conductive material to the antenna assembly, and a second layer applied over the first layer to ensure sealing to prevent fluid migration into the antenna body. Optionally, after the barrier layer has been applied, a portion of the conductive material (e.g., a distal end of the conductive material) is sealed with or otherwise coupled to a plug. The plug can be made of a non-conductive material, such as glue or another adhesive, a conformal coating (e.g., a parylene coating or vapor-deposited coating), or a reflowable material. The plug can be placed inside the barrier layer such that the barrier layer extends partially or entirely over the conductive material and the plug.

At optional step 760, a flexible instrument (e.g., flexible instrument 100 or 200 (FIG. 2)) can be inserted into a sheath (e.g., sheath 302, 402, or 504 of FIG. 3, 4, or 5, respectively). The flexible instrument can include the antenna assembly, the transmission member, and the barrier layer. At optional step 770, one or more fluid conduits (e.g., fluid conduit 304, 404, 504, 604*a*, 604*b*) can be inserted into the sheath. In some embodiments, steps 760 and 770 can be performed simultaneously. At step 780, proximal end components, such as components of a fluid cooling system (e.g., fluid cooling system 306, 406, or 506) or other component such as handles, connectors, etc. can be coupled to a proximal end portion of the flexible instrument.

Although the steps of the method 700 are discussed and illustrated in a particular order, the method 700 illustrated in FIG. 7 is not so limited. In other embodiments, for example, the method 700 can be performed in a different order (e.g., step 740 can be performed before step 720 and/or step 730). In these and other embodiments, any of the steps of the method 700 can be performed before, during, and/or after any of the other steps of the method 700. Moreover, a person of ordinary skill in the relevant art will recognize that the illustrated method 700 can be altered and still remain within these and other embodiments of the present technology. For example, one or more steps of the method 700 illustrated in FIG. 7 can be omitted (e.g., steps 740, 760, and/or 770) and/or repeated in some embodiments. For example, step 770 can be omitted in embodiments where the energy delivery system is a non-cooled system. Optionally, steps 760 and 770 can be omitted in embodiments where the flexible instrument is intended to be used without a sheath.

FIG. 8 is a flow diagram illustrating a method 800 of operating an energy delivery system in accordance with an embodiment of the present technology. The method 800 is illustrated as a set of steps, operations, or processes 810-850. In some embodiments, one or more of the steps 810-850 may be implemented, at least in part, in the form of executable code stored on non-transitory, tangible, machine-readable media. All or a subset of the steps 810-850 of the method 800 can be executed at least in part by various components or devices of an energy delivery system, such as any of the embodiments described above with respect to FIGS. 1-6B. For example, all or a subset of the steps 810-850 can be executed at least in part by components or devices of (i) a flexible instrument, (ii) an antenna assembly, (iii) a transmission member, (iv) one or more fluid conduits, and/or (v) a fluid cooling system. Additionally, or alternatively, all or a subset of the steps 810-850 of the method 800 can be executed at least in part by an operator (e.g., a physician, a user, etc.) of the energy delivery system, and/or by a robotically controlled surgical system via user inputs from the operator through a user input device or automatically through using closed loop control and/or pre-programmed instructions through a processor of the robotically controlled surgical system. Furthermore, any one or more of the steps 810-850 of the method 800 can be executed in accordance with the discussion above.

The method 800 begins at step 810 with delivering an energy delivery system (e.g. energy delivery system 300, 400, or 500 of FIG. 3, 4, or 5, respectively) at or near a target site within a patient's anatomy. The target site can be within an airway of the lungs of the patient. In some embodiments, the target site is a tumor within the airway or another anatomical region. As described above, delivering the energy delivery system can involve navigating the complex, tortuous patient anatomy until the distal portion of the energy delivery system is at a desired location, and then orienting the energy delivery system toward the target site or tumor. In some embodiments, delivery of the energy delivery system may be performed manually, the energy delivery system may be robotically controlled by user control through an input device, or the energy delivery system may be robotically controlled automatically using a pre-programmed set of instructions from a robotic system such as robotic medical systems described in detail below. In some embodiments the energy delivery system is delivered within a separate manual device or with the robotic medical system.

At step 820, once the distal portion of the energy delivery system is positioned and oriented appropriately within the airway, the method 800 can optionally include delivering a coolant (e.g., fluid 314, 414, or 514 of FIG. 3, 4, or 5, respectively) to cool at least a portion of the flexible instrument (e.g., to the distal portion and/or to an antenna assembly). The coolant can be used to cool the antenna assembly (e.g., antenna assembly 104) of the flexible instrument. The coolant can also be circulated to dissipate heat from tissue at the target site and/or from the transmission member (e.g., transmission member 102) of the flexible instrument. In some embodiments, the flexible instrument is positioned within a central lumen (e.g. central lumen 308, 408, or 508 of FIG. 3, 4, or 5, respectively) of a sheath, and a fluid cooling system (e.g., fluid cooling system 306, 406, or 506) and/or one or more fluid conduits (e.g., fluid conduit 304, 404, 504, 604*a*, 604*b*) could be used to deliver the coolant near a distal tip (e.g. distal tip 110 of FIG. 3, 4, or 5) of the flexible instrument. The coolant can be circulated around the distal tip, and return through the central lumen to exit the sheath. In some embodiments, the coolant can be delivered via one or more slots patterned into a fluid conduit and/or be purged from the sheath via one or more slots patterned within the sheath. In some embodiments, step 820 may be performed simultaneously with step 810. In alternative embodiments, step 820 may be performed before step 810, e.g. immediately before energy delivery, immediately upon positioning of the energy delivery system towards the target, or during a setup stage before the energy delivery system is inserted into patient anatomy. Additionally, step 820 may be omitted in embodiments where the energy delivery system is a non-cooled system.

At step 830, the method 800 optionally includes inserting the energy delivery system into tissue. For example, step 830 can include puncturing an airway wall with a tip section (e.g., tip section 312, 412, or 512 of FIG. 3, 4, or 5, respectively) of a sheath containing the flexible instrument, and positioning the portion of the sheath containing the antenna assembly at the target site (e.g., within the target tumor or lesion). Alternatively, the flexible instrument can be used to puncture the airway wall without using any sheath. As explained above, the distal end portion of the flexible instrument and/or sheath can have sufficient axial rigidity to puncture tissue without buckling or kinking. The rigidity of the flexible instrument can be increased, for example, by reinforcing the antenna assembly with inserts (e.g., inserts 128) and/or one or more material layers (e.g., jacket layer 122, barrier layer 130), as previously described. In an alternative embodiment, a separate puncturing device, such as a needle, can be used to make an initial puncture of the airway wall. The needle can be removed and the energy delivery system can be inserted into an opening created by the needle in the airway wall. In some embodiments, the positioning of the energy delivery system may be performed manually, the energy delivery system may be robotically controlled by user control through an input device, or the energy delivery system may be robotically controlled automatically using a pre-programmed set of instructions from a robotic system. In some embodiments the energy delivery system is delivered within a separate delivery device such as a manual flexible device or a flexible device controlled by a robotic medical system. The delivery device of the robotic medical system can be positioned in a stationary pose directed towards the target site, and the energy delivery system can be inserted through delivery device to be inserted within the tissue. In some embodiments, step 830 may be performed before or simultaneously with step 820.

At step 840, the method 800 continues with delivering energy through the transmission member to the antenna assembly (e.g., using a generator electrically coupled to the transmission member) to ablate tissue at the target site (e.g., the tumor). Once ablation is complete (e.g., once tumor/lesion and tissue margins have been adequately ablated as confirmed by sensor feedback such as impedance, temperature, imaging, and/or the like or once a pre-determined period of time has elapsed), the method 800 continues to step 850. At step 850, once ablation is complete, ablation energy delivery can be terminated, coolant delivery can be terminated, and/or the energy delivery system may be retracted and removed from patient anatomy. In some embodiments, the energy delivery system may be retracted manually, the energy delivery system may be robotically retracted by user control through an input device, or the energy delivery system may be robotically retracted automatically.

Although the steps of the method 800 are discussed and illustrated in a particular order, the method 800 illustrated in FIG. 8 is not so limited. In other embodiments, the method 800 can be performed in a different order. In these and other embodiments, any of the steps of the method 800 can be performed before, during, and/or after any of the other steps of the method 800. Moreover, a person of ordinary skill in the relevant art will recognize that the illustrated method 800 can be altered and still remain within these and other embodiments of the present technology. For example, one or more steps of the method 800 illustrated in FIG. 8 can be omitted and/or repeated in some embodiments.

Figure 9A:
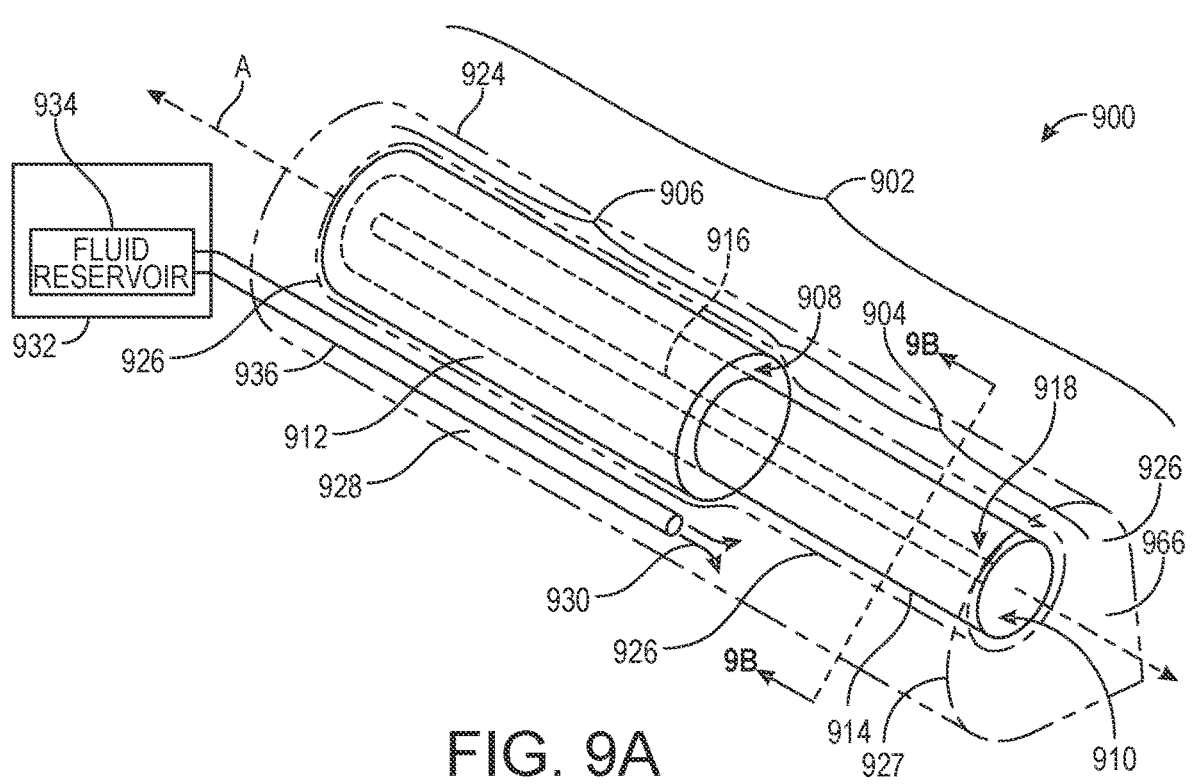
FIG. 9A is a perspective view of an energy delivery system for tissue ablation configured in accordance with various embodiments of the present technology.

FIGS. 9A-14B illustrate additional energy delivery systems configured in accordance with embodiments of the present technology, and can include a number of features, materials, and/or components similar to or identical to the energy delivery systems described above. FIG. 9A, for example, is a perspective view of an energy delivery system 900 for tissue ablation configured in accordance with various embodiments of the present technology. As shown in FIG. 9A, the energy delivery system 900 generally includes a flexible instrument 902 and a fluid cooling system 932. The flexible instrument 902 includes an antenna 904 and an elongate transmission member 906 positioned within a sheath 924. The antenna 904 extends distally from the elongate transmission member 906 between a proximal end portion 908 and a distal end portion 910. The elongate transmission member 906 includes an outer conductor 912 at least partially surrounding an inner conductor 916, and an insulator 914 (e.g., a dielectric layer) substantially surrounding the inner conductor 916 to insulate the outer conductor 912 from the inner conductor 916. In the illustrated embodiment, a portion 918 of the insulator 914 and the inner conductor 916 extend distally beyond the outer conductor 912 and form part of the antenna 904. Additionally, the elongate transmission member 906 is illustrated as a coaxial cable, but jacket layers and other details may not be illustrated for simplicity. For example, in some embodiments, the transmission member 906 can further include a protective or insulative layer (not shown) surrounding the outer conductor 912 (e.g., to provide structural integrity to the outer conductor 912). Other coaxial cable configurations with different configurations, shapes, etc. of inner conductor, outer conductor, and dielectric layers could also be used. In alternative embodiments, any type of elongate transmission member 906 may be used for the flexible instrument 902.

In accordance with embodiments of the present technology, the antenna 904 can be one of various types of antennas known in the art. For example, the antenna 904 can be a helical dipole antenna as shown and described in greater detail in U.S. patent application Ser. No. 16/670,847 filed Oct. 31, 2019 disclosing "Coiled Dipole Antenna", or U.S. patent application Ser. No. 16/670,947 filed Oct. 31, 2019 disclosing "Coiled Antenna with Fluid Cooling," which are both incorporated by reference herein in their entirety. In other embodiments, the antenna 904 can be a patterned tube antenna as shown and described in greater detail in PCT Patent App. No. PCT/US19/24564 filed Mar. 28, 2019 disclosing "Systems and Methods Related to Flexible Antennas" which is incorporated by reference herein in its entirety. In other embodiments, the antenna 904 can be a double helical, slot, dual slot, monopole, solid tube or another type of antenna. In the illustrated embodiment, the antenna 904 extends along a longitudinal axis A and includes the portion 918 of the inner conductor 916 that extends distally beyond the outer conductor 912. The antenna 904 can be used to radiate microwave energy for use in the tissue ablation process. More specifically, the antenna 904 is used to create electromagnetic radiation within a wavelength range of one meter to one millimeter, and within a frequency range of approximately 300 Megahertz (MHz) to 300 Gigahertz (GHz) (e.g., a microwave). In some embodiments, the wavelength and the frequency of the microwaves being radiated by the antenna 904 may be modified to cause a desired type of ablation at the ablation target site.

In some embodiments, the material of the insulator 914 may be chosen to provide a high axial stiffness along the axis A to allow greater rigidity to puncture tissue. Rigid materials such as PEEK or polyetherimide (such as those manufactured by SABIC of Riyadh, Saudi Arabia and sold under the trademark ULTEM) may be used, for example, to increase stiffness in the antenna and prevent buckling or kinking during a puncture operation.

Figure 9B:
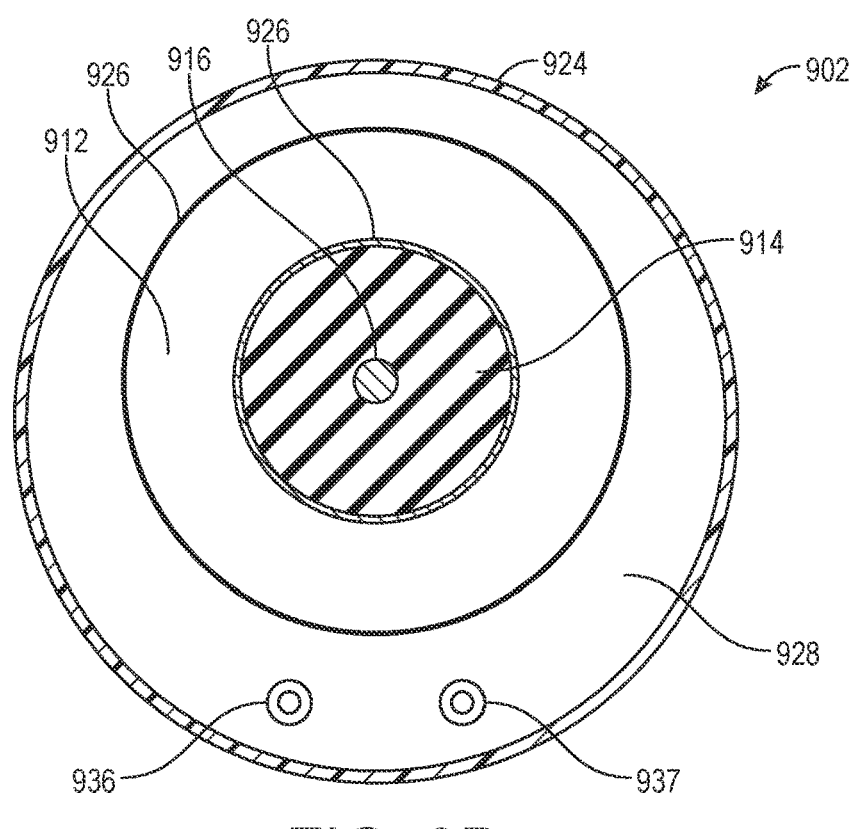
FIG. 9B is a cross-sectional end view of a flexible instrument of the energy delivery system of FIG. 9A configured in accordance with various embodiments of the present technology.

FIG. 9B is a cross-sectional end view of the energy delivery system 900 taken along line 9B-9B of FIG. 9A. Referring to FIGS. 9A and 9B together, the energy delivery system 900 in some embodiments can include a barrier layer 926 that extends along the flexible instrument 902, creating a barrier or seal to prevent inward migration of fluid. The barrier layer 926 may be formed of a thermoplastic such as polyethylene terephthalate (PET) or other flexible and fluid insulating and impermeable materials. The barrier layer 926 may be thin and form fit around the components of the flexible instrument 902 or may maintain a flexible tubular form. In some embodiments, the barrier layer 926 may provide added rigidity to support the antenna 904.

In the illustrated embodiment, the antenna 904 and the transmission member 906 are disposed within the sheath 924. In some embodiments, the sheath 924 is closed, sealed, or otherwise restricts fluid from passing into or out of the sheath 924. For example, the sheath 924 may optionally be coupled to and/or sealed by a tip section 966 (FIG. 9A) at a distal end 927 (FIG. 9A) of the sheath 924. The sheath 924 and tip section 966 can be identical or generally similar to the sheath 302 and tip section 166, respectively, of FIG. 3.

A chamber or channel 928 is formed between the sheath 924 and the barrier layer 926 and receives a coolant (e.g., a fluid 930 (FIG. 9A) or other cooling agent, such as gas) to cool the flexible instrument 902. The fluid 930 may be, for example, water or a saline solution. The fluid 930 may be provided to the channel 928 from a fluid cooling system 932 (FIG. 9A) coupled to the channel 928. The fluid cooling system 932 may be identical or generally similar to the fluid cooling system 306 of FIG. 3. In the illustrated embodiment, the fluid cooling system 932 also includes or is coupled to fluid conduits 936 and 937 (FIG. 9B) that extend through at least a portion of the channel 928 and run alongside at least the transmission member 906 (FIG. 9A) within the sheath 924. The coolant may be directed within the channel 928 through the fluid conduit 936 and/or through the fluid conduit 937. Each of the fluid conduits 936, 937, for example, may be identical or generally similar to the fluid conduit 304 of FIG. 3.

The fluid conduit 936 and/or the fluid conduit 937 may be used, for example, to provide inflow of the fluid 930 to the channel 928. The fluid 930 can circulate about the antenna 904 and/or the transmission member 906 within the channel 928, and can return in a proximal direction within the channel 928 to be purged in a reservoir (not shown) or purged to the environment. In another embodiment, the fluid 930 can exit the sheath 924 via openings or slits in the sheath 924 or return to a fluid cooling system 932 via the channel 928 and/or another fluid conduit (not shown). Alternatively, the fluid conduit 936 and/or 937 can be used to provide return flow of the fluid 930 from the channel 928 by discontinuing inlet fluid from the fluid reservoir 934, reversing flow and providing suction to the fluid conduit 936 and/or 937 using the fluid cooling system. In another embodiment, a separate fluid conduit (not shown) can be provided that does not provide inflow of fluid 930 and is only used for return flow. In some embodiments, the return flow can be purged in a combination of flow through the channel 928 in a proximal direction, flow through fluid conduits, and through openings in sheath 924.

In the illustrated embodiment, the fluid conduits 936 and 937 are separate from one another such that each can flex independently of one another when the flexible instrument is navigated to a target. In some embodiments, separate fluid conduits provide greater recoverable flexibility and/or axial rigidity than fluid conduits that are attached to one another. In other embodiments of the present technology, however, the fluid conduits 936 and 937 can be joined to one another and/or can be formed as a single structure.

Although the energy delivery system 900 is illustrated in FIGS. 9A and 9B with two circular fluid conduits 936 and 937 that run alongside the off-centered transmission member 906 (FIG. 9A), energy delivery systems configured in accordance with other embodiments of the present technology can include a different number, shape, and/or position of fluid conduits. For example, an energy delivery system of the present technology can include one, or three or more fluid conduits in some embodiments. In some embodiments, a single fluid conduit may result in an unbalanced device or size requirements, and high frictional losses (high pressure drops due to added wall thickness of additional fluid conduits) may limit the number of fluid conduits to three or less. The transmission member 906 may be centered within the channel 928 and the fluid conduits may be distributed evenly or un-evenly around the transmission member 906. Additionally, or alternatively, all or a subset of the fluid conduits can have a non-circular (e.g., a "D"-shaped, a rectangular, etc.) cross-sectional shape. In some embodiments with a single fluid conduit, the fluid conduit can be irregularly shaped to balance the symmetry of the design. In these and still other embodiments, at least one fluid conduit can be positioned concentric with the transmission member 906 (e.g., surrounding the inner conductor 916, the insulator 914, the outer conductor 912, and/or the transmission member 906) within the sheath 924 and terminate at or near the proximal end 908 of the antenna 904. A minimum wall thickness of the fluid conduits 936 and/or 937 may be necessary to prevent kinking of the channel 928. The wall thickness may, however, limit the overall cross-sectional area of other components within the device in order to maintain a desired total outer diameter.

As described previously, the flexible instrument 902 (and associated fluid conduits 936 and 937) must be sufficiently flexible to navigate tortuous anatomical passageways and facilitate delivery of the flexible instrument 902 to a target site within patient anatomy. The flexible instrument 902 and fluid conduits 936 and 937 may be identical or generally similar to the flexible instrument 302 and fluid conduit(s) 304 described above with reference to FIG. 3 and have many or all of the same features and advantages. For example, the fluid conduits 936 and/or 937 can be formed of a resiliently flexible material (e.g., nitinol or another suitable shape memory material). If constructed from nitinol, the fluid conduit can be laser cut or ground to adjust stiffness over the length of the fluid conduits 936 and/or 937. In some embodiments, a fluorinated ethylene propylene (FEP) layer may surround the fluid conduit 936 and/or the fluid conduit 937. In still further embodiments, the fluid conduits 936 and/or 937 may be constructed entirely from a polymer material (and not include nitinol).

FIGS. 10-13, 14A, and 14B are cross-sectional side views of energy delivery systems 1000, 1100, 1200, 1300, and 1400, respectively, for tissue ablation configured in accordance with various embodiments of the present technology. The energy delivery systems 1000-1300 and 1400 of FIGS. 10-13, 14A, and 14B are similar to the energy delivery system 900 of FIG. 9 with exception to differences disclosed herein. Thus, like reference numerals are used to identify like elements illustrated in FIGS. 9-14B. Furthermore, FIGS. 10-14B are each discussed in detail below with reference to a single fluid conduit. A person of ordinary skill in the art will readily appreciate, however, that any of the energy delivery systems 1000-1300 and 1400 described below can include multiple fluid conduits and that all or a subset of the fluid conduits of each system 1000-1300 and 1400 can share one or more of the features of the fluid conduits described herein.

Figures 10, 11:
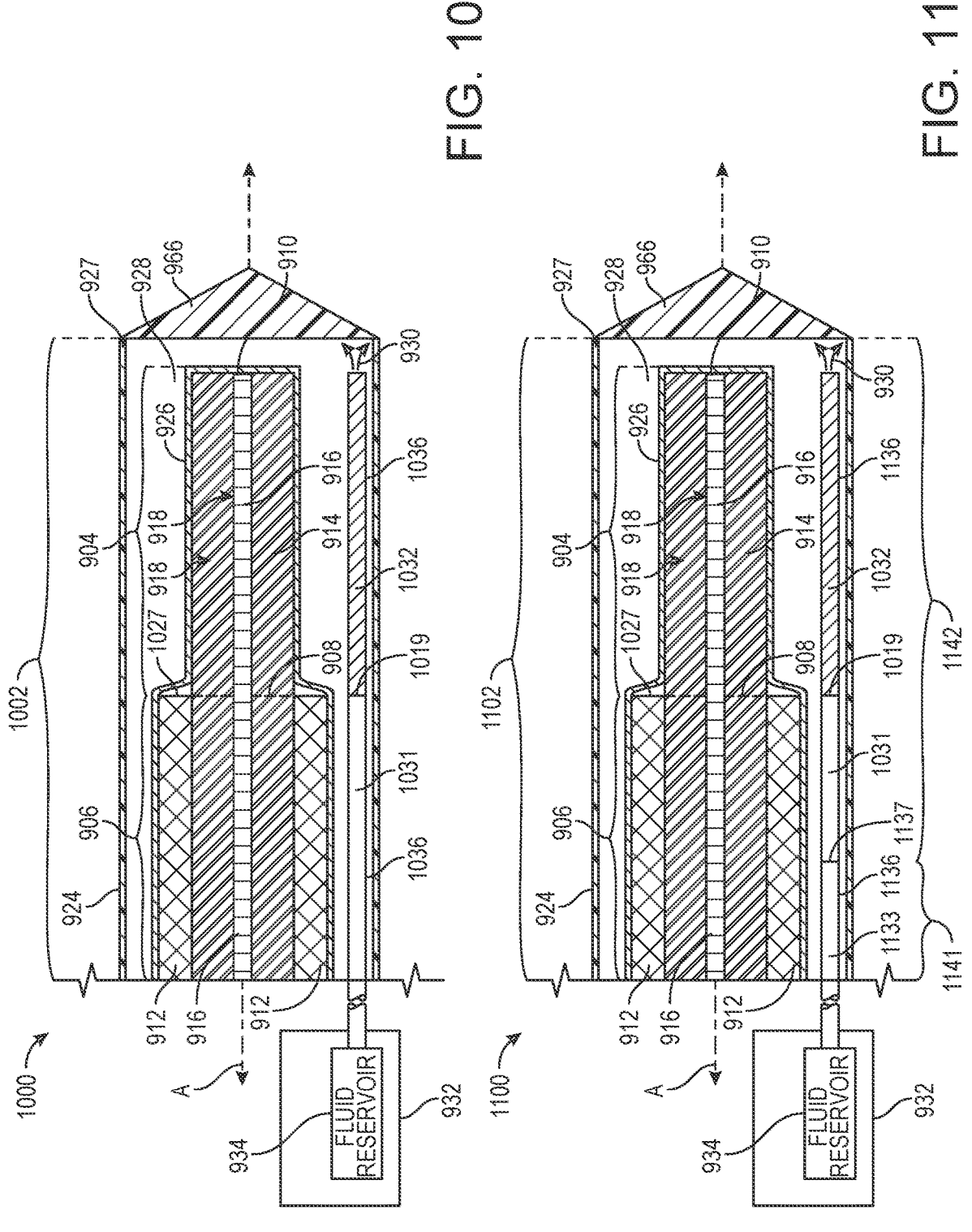
FIG. 10 is a cross-sectional side view of an energy delivery system for tissue ablation configured in accordance with various embodiments of the present technology.
FIG. 11 is a cross-sectional side view of an energy delivery system for tissue ablation configured in accordance with various embodiments of the present technology.

Referring to FIG. 10, the energy delivery system 1000 includes a flexible instrument 1002 having antenna 904, elongate transmission member 906, and a fluid conduit 1036 disposed within sheath 924. Barrier layer 926 extends along the flexible instrument 1002, creating a barrier or seal to prevent inward migration of fluid. As mentioned previously, the barrier layer 926 may be thin and form fit (e.g. heat shrink) around components (e.g., the antenna 904, the transmission member 906, etc.) of the flexible instrument 1002 or may maintain a flexible tubular form.

As discussed above, channel 928 is formed between the sheath 924 and the barrier layer 926 and receives fluid flow of fluid 930 (e.g., a coolant such as saline, water, or another cooling agent, such as gas) to cool the flexible instrument 1002. In the illustrated embodiment, the antenna 904 terminates before the distal end 927 of the sheath 924 such that the channel 928 surrounds the distal end portion 910 of the antenna 904. In other embodiments, the antenna 904 can extend to the distal end 927 of the sheath 924 such that the channel 928 does not surround the distal end portion 910 of the antenna 904 within the sheath 924.

The fluid conduit 1036 can be identical or generally identical to the fluid conduit 304 described above with reference to FIG. 3, and can be fabricated using the same or similar techniques and/or materials. In the illustrated embodiment, for example, the fluid conduit 1036 includes a first region 1031 and a second region 1032. The fluid conduit 1036 extends through at least a portion of the channel 928 and runs alongside the transmission member 906 within the sheath 924, terminating near the distal end portion 910 of the antenna 904. Extending the fluid conduit 1036 to at least the distal end portion 910 of the antenna 904 can provide an added benefit of delivering coolant to the distal end portion 910 of the antenna for increased and/or more uniform cooling of the antenna 904. Additionally, terminating the fluid conduit 1036 near a proximal end portion 908 of antenna 904 (as illustrated in FIG. 9A) leaves the portion of the flexible instrument 1002 from the proximal end portion 908 of the antenna 904 to the distal end portion 927 of the sheath 924 unsupported by the fluid conduit 1036, reducing axial stiffness of the flexible instrument 1002 along the axis A. In addition, a point of weakness can be created along the flexible instrument 1002 at or near the proximal end portion 908 of the antenna 904 where the first region 1031 of the fluid conduit 1036 terminates. Such a point of weakness can reduce the bend radius of the flexible instrument 1002 during delivery of the antenna 904 through patient anatomy and can increase the likelihood of the flexible instrument 1002 buckling or kinking along the unsupported portion during a puncture operation (especially if the antenna 904 is off-centered within the sheath 924).

As previously described, forming the fluid conduit 1036 of a shape memory material can provide (i) the flexibility (e.g., the deformability) required to facilitate delivery of the flexible instrument 1002 through tortuous patient anatomy and (ii) the resiliency (e.g., recoverability, spring back, etc.) required to return the fluid conduit 1036 (and therefore the flexible instrument 1002) to its initial (e.g., undeformed) state or shape after deformation to reduce trajectory error and facilitate accurate delivery of the antenna 904 to the target site during a puncture operation. However, many shape memory and other resiliently flexible materials (including nitinol) are conductive at the frequency range (e.g., 300 MHz to 300 GHz) of the microwave antenna 904, meaning that any region of the fluid conduit 1036 that runs alongside the antenna 904 within the sheath 924 and is formed of a conductive material would interfere with the antenna 904 during energy delivery.

Accordingly, the first region 1031 of the fluid conduit 1036 can be formed of a shape memory material, such as nitinol, and extend along the elongate transmission member 906, whereas the second region 1032 of the fluid conduit 1036 can be formed of a non-conductive material, such as a plastic or polymer, and extend along the antenna 904. As illustrated in FIG. 10, the first region 1031 terminates at a point along the length of the flexible instrument 1002 proximal the proximal end portion 908 of the antenna 904 such that the first region 1031 does not interfere with the antenna 904 during energy delivery. The second region 1032 can terminate at or near the distal end portion 910 of the antenna 904 or can extend to the distal end portion 927 of the sheath 924 (e.g., to provide stiffness and axial rigidity along the entire length of the flexible instrument 1002). Because the second region 1032 of the fluid conduit 1036 is formed of a material that is non-conductive at the frequency range of the antenna 904, the second region 1032 does not interfere with the antenna 904 during energy delivery.

FIG. 11 is a cross-sectional view of an energy delivery system 1100 having a flexible instrument 1102 configured in accordance with another embodiment of the present technology. The energy delivery system 1100 and the flexible instrument 1102 are similar to the energy delivery system 1000 and the flexible instrument 1002, respectively, of FIG. 10 except that the fluid conduit 1136 of the flexible instrument 1102 illustrated in FIG. 11 includes a third region 1133 proximal the first region 1031.

As illustrated in FIG. 11, the flexible instrument 1102 includes a proximal section 1141 and a distal section 1142. The distal section 1142 extends distally from the proximal section 1141 at a point along the length of the transmission member 906 to at least the distal end portion 910 of the antenna 904 (e.g., to the distal end 927 of the sheath 924). The third region 1133 of the fluid conduit 1136 can extend along at least a portion of the proximal section 1141 of the flexible instrument 1102, while the first region 1031 of the fluid conduit 1136 can extend along at least a portion of the distal section 1142 of the flexible instrument 1102 to provide recoverable flexibility along this portion of the flexible instrument 1102. The second region 1032 of the fluid conduit 1136 can extend along the antenna 904, terminating at distal end portion 910 of antenna 904. In some embodiments, the various regions/sections of the fluid conduit 1136 may be fabricated using materials and techniques similar to or identical to those described above with reference to FIG. 4.

Figures 12, 13:
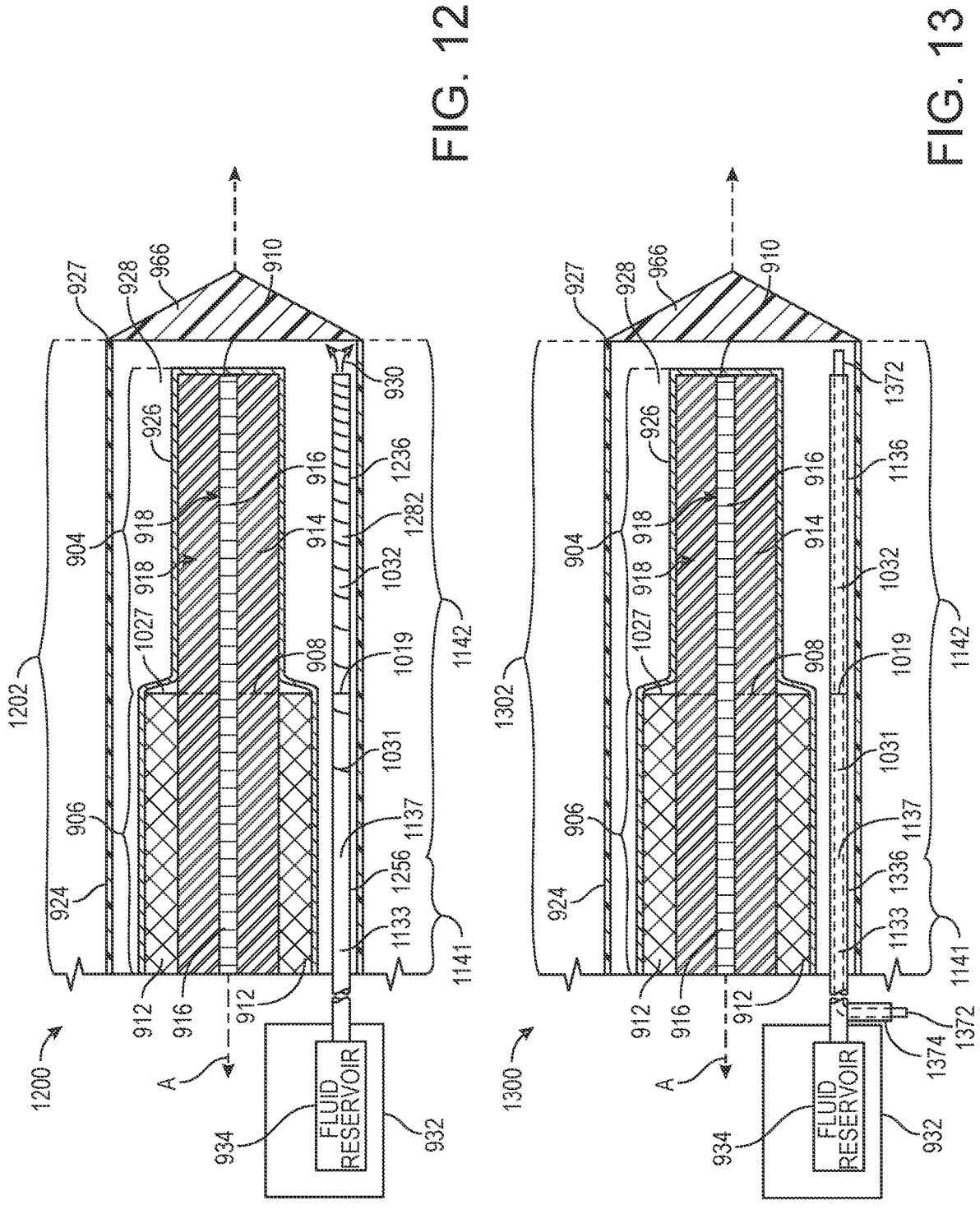
FIG. 12 is a cross-sectional side view of an energy delivery system for tissue ablation configured in accordance with various embodiments of the present technology.
FIG. 13 is a cross-sectional side view of an energy delivery system for tissue ablation configured in accordance with various embodiments of the present technology.

FIG. 12 is a cross-sectional view of an energy delivery system 1200 having a flexible instrument 1202 configured in accordance with another embodiment of the present technology. The energy delivery system 1200 and the flexible instrument 1202 are similar to the energy delivery systems 900/1000/1100/1200 and the flexible instruments 902/1002/1102, respectively, of FIGS. 9/10/11 except that the flexible instrument 1202 illustrated in FIG. 12 comprises a fluid conduit 1236 that is patterned with slots 1282 (e.g., cutouts, slits, etc.). In particular, both the first region 1031 and the second region 1032 of the fluid conduit 1236 include a gradient of slots 1282 along their lengths to vary the stiffness of the corresponding regions 1031 and 1032 of the fluid conduit 1236.

In some embodiments, the slots/openings of fluid conduit 1236 can be generally similar to or identical to the slots described above with reference to FIGS. 5-6B. Further, as described above with reference to FIG. 5, one or more of the slots in some embodiments can serve as points of exit for a coolant (e.g., a fluid or gas) to exit the fluid conduit 1236 and enter the channel (or vice versa). In further embodiments, patterned slots as described above can be included at any point of weakness along the flexible instrument. For example, the change in diameters between the outer conductor 912 and the inner conductor 916 could result in a point of weakness. In this case, a set of patterned slots can be utilized to create a more gradual transition between these components. Other points of weakness can occur at transitions between different materials. Accordingly, in an embodiment where the materials of the outer conductor 912, the inner conductor 916, the dielectric material 914, and/or the fluid conduits 1236 are not uniform, any transition between different materials could be considered a point of weakness and patterned slots can be utilized to make the transition gradual, thereby reducing or eliminating the point of weakness.

FIG. 13 is a cross-sectional view of an energy delivery system 1300 having a flexible instrument 1302 configured in accordance with still another embodiment of the present technology. The energy delivery system 1300 and the flexible instrument 1302 are similar to the energy delivery system 1000 and the flexible instrument 1002, respectively, of FIG. 10 except that the flexible instrument 1302 illustrated in FIG. 13 comprises a fluid conduit 1336 formed of a continuous material along its entire length. In some embodiments, for example, the fluid conduit 1336 is formed of a material that is non-conductive at the frequency range of the antenna 904 such that the fluid conduit 1336 does not interfere with the antenna 904 during energy delivery. For example, the fluid conduit 1336 can be formed of a plastic, polymer, or other non-conductive material. In the illustrated embodiment, the fluid conduit 1336 runs along substantially the entire length of the flexible instrument 1302 from a proximal end portion of the flexible instrument 1302 to at least the distal end portion 910 of the antenna 904.

To provide recoverable flexibility and/or axial stiffness to the flexible instrument 1302 during delivery of the flexible instrument 1302 to a target site through patient anatomy and/or during a puncture operation, a stylet 1372 can be inserted into a lumen of the fluid conduit 1336 (e.g., via a port or valve 1374 of the fluid conduit 1336) and extended to at least the distal end portion 910 of the antenna 904. In some embodiments, the stylet 1372 can be formed of a resiliently flexible material, such as nitinol or another shape memory material.

In some embodiments, the stylet 1372 and fluid conduit 1336 are sized to allow for space within the lumen of the fluid conduit so that a coolant (e.g., a cooling fluid or gas) can be delivered to or removed from the channel 928 via the fluid conduit 1336 and/or another fluid conduit (not shown) of the flexible instrument 1302 while the stylet 1372 is inserted into the fluid conduit 1336. In other embodiments, the stylet 1372 can be removed from the fluid conduit 1336 before transporting the coolant to or from the channel 928 via the fluid conduit 1336. For example, the stylet 1372 can be removed from the fluid conduit 1336 (e.g., via the port 1374) once the flexible instrument 1302 is positioned at a target site, and a coolant (not shown in FIG. 13) can subsequently be delivered to or removed from the channel 928 via the fluid conduit 1336 to cool the antenna 904, particularly during delivery of ablative energy.

In some embodiments, a proximal end portion of the stylet 1372 can be directly or indirectly connected to a slidable mechanism (not shown). The slidable mechanism can be configured to distally and/or proximally slide the stylet 1372 within the fluid conduit 1336. For example, the slidable mechanism can be robotically controlled to (e.g., automatically and/or in response to an operator command) extend the stylet 1372 into the fluid conduit 1336 before and/or during navigation of the flexible instrument 1302 and/or before and/or during a puncture operation using one or more actuators such as motors and/or motor driven leadscrews, a hydraulic system, a motor driven cable system, a robotic arm, and/or the like (not shown). Additionally, or alternatively, the slidable mechanism can be robotically controlled to (e.g., automatically and/or in response to an operator command) retract the stylet 1372 from the fluid conduit 1336 after the flexible instrument 1302 is positioned at a target site, before transporting coolant via the fluid conduit 1336, and/or before delivery energy via the antenna 904.

Figure 14A:
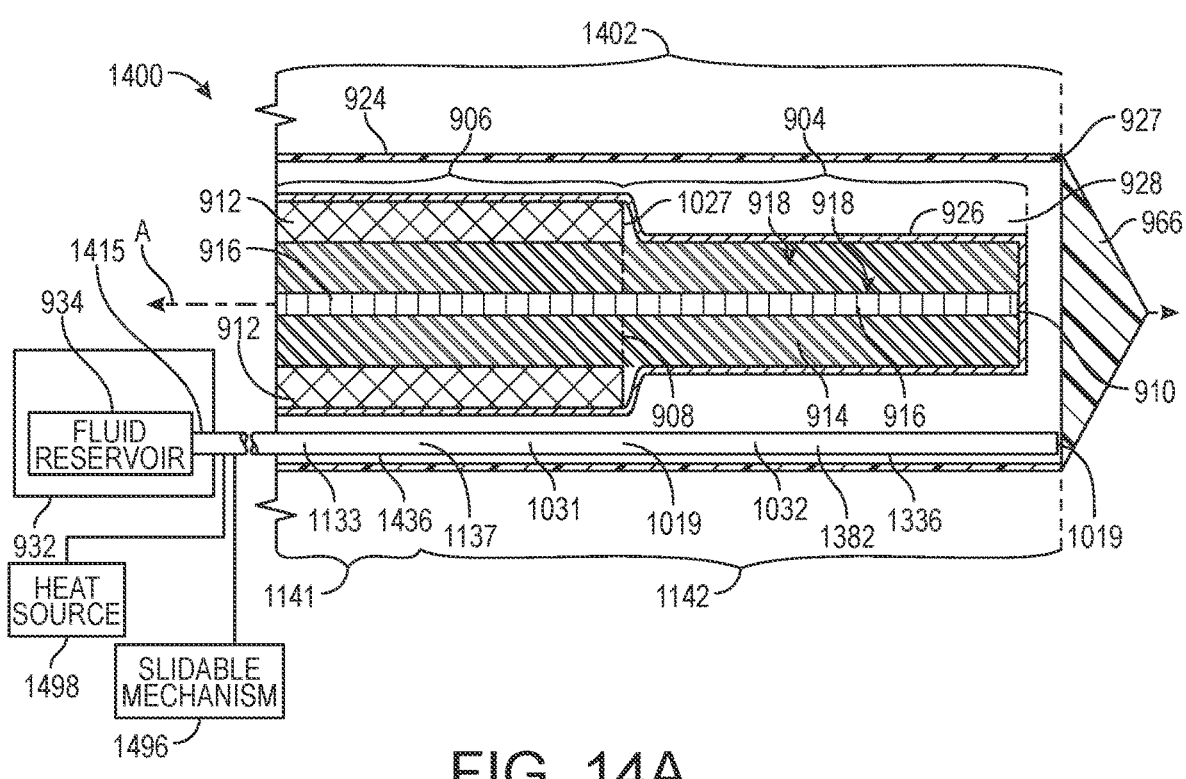
FIG. 14A is a cross-sectional side view of an energy delivery system for tissue ablation in a first state configured in accordance with various embodiments of the present technology.
Figure 14B:
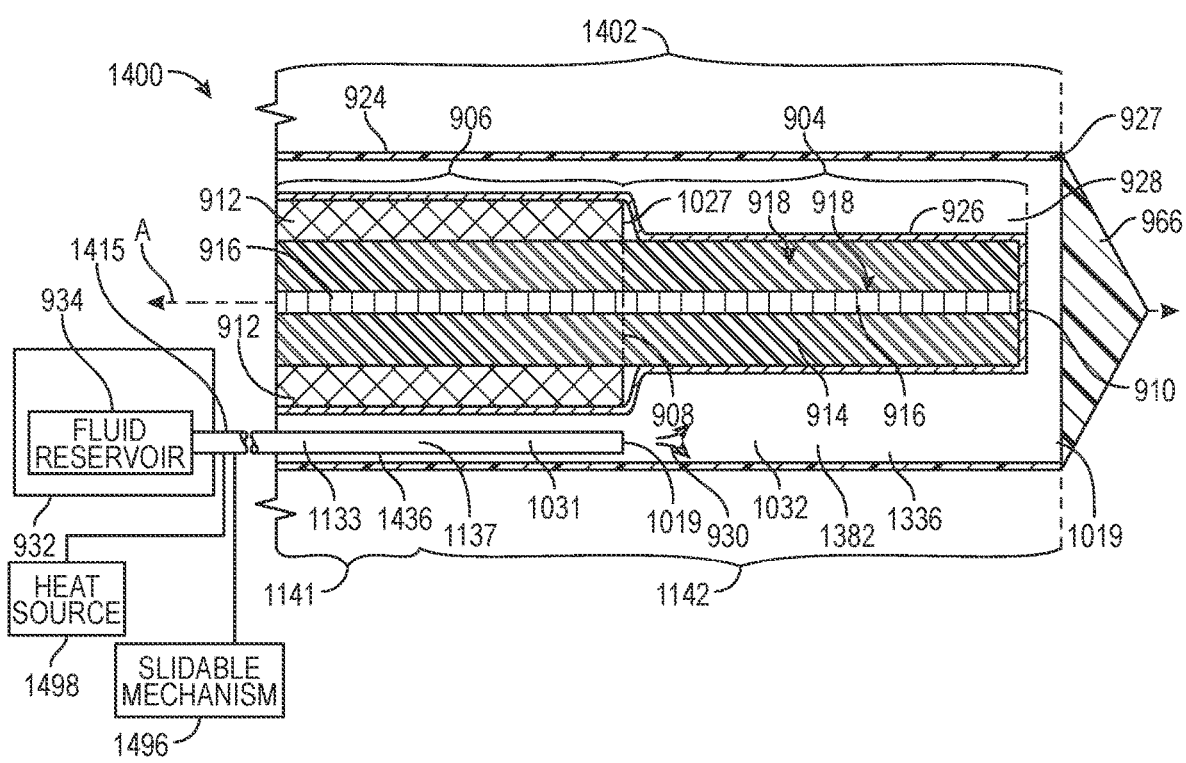
FIG. 14B is a cross-sectional side view of the energy delivery system of FIG. 14A in a second state configured in accordance with various embodiments of the present technology.

FIGS. 14A and 14B are cross-sectional views of an energy delivery system 1400 having a flexible instrument 1402 configured in accordance with a further embodiment of the present technology. The energy delivery system 1400 and the flexible instrument 1402 are similar to the energy delivery system 1100 and the flexible instrument 1102, respectively, of FIG. 11 except that the flexible instrument 1402 illustrated in FIG. 14 comprises a fluid conduit 1436 distally and proximally slidable within the sheath 924 in a direction parallel with axis A. In some embodiments, the fluid conduit 1436 may be formed of a single material similar to fluid conduit 1336 of FIG. 13. In alternative embodiments, the fluid conduit 1436 can be formed of more than one material similar to the fluid conduit 1136 of FIG. 11. For example, the fluid conduit 1436 can include a first region (e.g. similar to the first region 1031 of FIG. 11) formed of a resiliently flexible material, a second region (e.g., similar to the second region 1032 of FIG. 11) formed of a non-conductive material, and/or a third region (e.g., similar to the third region 1133 of FIG. 11) formed of a less expensive material (e.g., to reduce costs). In other embodiments and as shown in FIGS. 14A and 14B, the fluid conduit 1436 can be formed of a continuous material along its entire length, such as a resiliently flexible material (e.g. nitinol or another suitable shape memory material).

FIG. 14A illustrates the fluid conduit 1436 in a fully extended state. In particular, the fluid conduit 1436 can be slid distally within the sheath 924 in a direction parallel with the axis A until the distal end portion 1019 of the fluid conduit 1436 is positioned at or near the distal end portion 927 of the sheath 924. Alternatively, the fluid conduit 1436 can be slide distally within the sheath 924 until the distal end portion 1019 of the fluid conduit 1436 is positioned just short of the distal end portion 927 of the sheath 924 (e.g., at the distal end portion 910 of the antenna 904) to allow a coolant to enter/exit the fluid conduit 1436 from/into the channel 928.

In some embodiments, the fluid conduit 1436 can be positioned in the fully extended state while navigating the flexible instrument 1402 through patient anatomy (e.g., to provide recoverable flexibility) and/or while performing a puncture operation (e.g., to provide stiffness along the axis A and reduce the likelihood of the flexible instrument 1402 buckling or kinking at a point along its length). In one embodiment, a coolant (e.g., the fluid 930 shown in FIG. 14B or a gas) can be continually delivered to the channel 928 while the fluid conduit 1436 is in the fully extended state to provide additional stiffness to the flexible instrument 1402. In other embodiments, a coolant can be intermittently delivered to the channel 928 while the fluid conduit 1436 is in the fully extended state. For example, in one embodiment, coolant is not delivered to the channel 928 while navigating the flexible instrument 1402 through patient anatomy to maintain maximum flexibility of the flexible instrument 1402, but coolant is delivered to the channel 928 before and/or during a puncture operation to provide additional stiffness to the flexible instrument 1402. In still other embodiments, coolant is not provided to the channel 928 while the fluid conduit 1436 is in the fully extended state.

FIG. 14B illustrates the fluid conduit 1436 in a retracted state. In particular, the fluid conduit 1436 can be slid proximally within the sheath 924 in a direction parallel with the axis A at least until the distal end portion 1019 of the fluid conduit 1436 is positioned proximal the proximal end portion 908 of the antenna 904 (e.g., at or near the distal end portion 1007 of the transmission member 906). In this manner, the fluid conduit 1436 can be retracted within the sheath 924 to a position where the fluid conduit 1436 will not interference with the antenna 904 during energy delivery. In some embodiments, the fluid conduit 1436 can be positioned in the fully retracted state after the flexible instrument 1402 is positioned at a target site and/or before delivering energy via the antenna 904. A coolant can then be delivered to or removed from the channel 928 via the fluid conduit 1436 to cool the antenna 904 during energy delivery.

Referring to FIGS. 14A and 14B together, the energy delivery system 1400 can further include a translation actuator in the form of a slidable mechanism 1496 and/or a heat source 1498. In some embodiments, the slidable mechanism 1496 can be directly or indirectly connected to a proximal end portion 1415 of the fluid conduit 1436 and configured to slide the fluid conduit 1436 distally and/or proximally within the jacket in a direction parallel with the axis A and between the fully extended and fully retracted states. For example, the proximal end portion 1415 of the fluid conduit 1436 can be translated in a direction parallel with the axis A using one or more actuators such as motors and/or motor driven leadscrews, a hydraulic system, a motor driven cable system, a robotic arm, and/or the like (not shown). In some embodiments the proximal end portion can be mounted on a linear slide (not shown) of the slidable mechanism 1496. In other embodiments, the proximal end portion is mounted to a robotic arm and translated in a parallel direction by actuating the robotic arm. In some embodiments, the slidable mechanism 1496 can be robotically controlled to (e.g., automatically and/or in response to an operator command) slide the fluid conduit 1436 distally within the sheath 924 before and/or during navigation of the flexible instrument 1402 through patient anatomy and/or before and/or during a puncture operation. Additionally, or alternatively, the slidable mechanism 1496 can be robotically controlled to (e.g., automatically and/or in response to an operator command) slide the fluid conduit 1436 proximally within the sheath 924 after delivery of the flexible instrument 1402 to a target site, before transporting a coolant via the fluid conduit 1336, and/or before delivering energy via the antenna 904. In some embodiments, the fluid cooling system 932 and proximal end portion 1415 are both mounted on the slidable mechanism 1436. In an alternative embodiment, only the proximal end portion 1415 is mounted on the slidable mechanism and a compliant coupling (not shown) couples the fluid conduit 1436 to the fluid cooling system 932 which is stationary relative to the proximal end portion 1415.

In these and other embodiments, the fluid conduit 1436 can be formed of a material (e.g., nitinol, shape memory polymer, a shape memory metal or alloy) that changes in shape (e.g., transforms between a first configuration and a second different configuration) in response to a stimulus (e.g., thermal energy, heat, mechanical loading). In one embodiment, for example, the fluid conduit 1436 can be anchored at a proximal end portion and heat can be applied to the fluid conduit 1436 to transform (e.g., contract, retract) the fluid conduit 1436 proximally within the sheath 924. In one example, thermal energy generated by the antenna 904 during energy delivery can activate a portion of the fluid conduit 1436 to transform (retract) proximally within the sheath 924 to an extent where the fluid conduit 1436 no longer overlaps with the antenna 904. The energy delivery can be altered such that a first frequency range is applied to retract the fluid conduit 1436. Subsequently, once the fluid conduit 1436 is retracted to a position where the fluid conduit 1436 does not overlap with antenna 904, a second frequency range is applied for tissue ablation. As another example, the heat source 1498 can (e.g., electrically) apply heat to the proximal end portion 1415 and/or to one or more other portions along the length of the fluid conduit 1436 (e.g., after the flexible instrument 1402 is positioned at a target site and/or before delivering energy via the antenna 904 and before delivering energy via the antenna 904) to retract the fluid conduit 1436 proximally within the sheath 924 to an extent where the fluid conduit 1436 does not overlap with the antenna 904.

FIG. 15 is a flow diagram illustrating a method 1500 for manufacturing an energy delivery system in accordance with various embodiments of the present technology. The method 1500 is illustrated as a set of steps, operations, or processes 1502-1512. At step 1502, the method 1500 begins with connecting a tip section (e.g., tip section 966) to or forming a tip section from a jacket (e.g., sheath 924). At step 1504, an antenna (e.g., antenna 904) can be formed at and/or be connected to a distal end of a transmission member (e.g., transmission member 906). At step 1506, a barrier layer (e.g., barrier layer 926) can be extended over the antenna and the transmission member. At step 1508, the antenna, the transmission member, and the barrier layer can be inserted into a central lumen of the jacket. At step 1510, one or more fluid conduit(s) (e.g., fluid conduit 936, 937, 1036, 1136, 1236, 1336, and/or 1436) can be inserted into the central lumen of the jacket to form a flexible instrument (e.g., flexible instrument 902, 1002, 1102, 1202, 1302, and/or 1402). In some embodiments, steps 1508 and 1510 can be performed simultaneously. At step 1512, proximal end components (e.g., components of a fluid cooling system (e.g., fluid cooling system 932), components of a slidable mechanism (e.g., slidable mechanism 1496), components of a heat source (e.g., heat source 1498), handles, connectors, etc.) can be coupled to a proximal end portion of the flexible instrument.

Although the steps of the method 1500 are discussed and illustrated in a particular order, the method 1500 illustrated in FIG. 15 is not so limited. In other embodiments, the method 1500 can be performed in a different order. In these and other embodiments, any of the steps of the method 1500 can be performed before, during, and/or after any of the other steps of the method 1500. Moreover, a person of ordinary skill in the relevant art will recognize that the illustrated method 1500 can be altered and still remain within these and other embodiments of the present technology. For example, one or more steps of the method 1500 illustrated in FIG. 15 can be omitted and/or repeated in some embodiments.

FIG. 16 is a flow diagram illustrating a method 1600 of operating an energy delivery system in accordance with various embodiments of the present technology. The method 1600 is illustrated as a set of steps, operations, or processes 1601-1612. In some embodiments, one or more of the steps 1601-1612 may be implemented, at least in part, in the form of executable code stored on non-transitory, tangible, machine-readable media. All or a subset of the steps 1601-1612 of the method 1600 can be executed at least in part by various components or devices of an energy delivery system, such as any of the energy delivery systems described above with respect to FIGS. 9-15. For example, all or a subset of the steps 1601-1612 can be executed at least in part by components or devices of (i) a fluid cooling system, (ii) a flexible instrument, (iii) a transmission member, (iv) an antenna, (v) one or more fluid conduits, (vi) a stylet, (vii) a translation actuator, (viii) a slidable mechanism, and/or (ix) a heat source. Additionally, or alternatively, all or a subset of the steps 1601-1612 of the method 1600 can be executed at least in part by an operator (e.g., a physician, a user, etc.) of the energy delivery system, and/or by a robotically controlled surgical system via user inputs from the operator through a user input device or automatically through using closed loop control and/or pre-programmed instructions through a processor of the robotically controlled surgical system. Furthermore, any one or more of the steps 1601-1612 of the method 1600 can be executed in accordance with the discussion above.

The method 1600 begins at step 1601 with positioning a sliding element in a fully extended position within a flexible instrument. As discussed previously, at least a distal section of the flexible instrument can undergo substantial deformation during navigation of the patient anatomy. As such, the flexible instrument must be flexible enough to navigate patient anatomy, yet resilient enough to return to an initial (e.g., undeformed) state or shape after deformation. Accordingly, positioning the sliding element in a fully extended position within the flexible instrument provides recoverable flexibility to the flexible instrument. For example, the sliding element may include a fluid conduit slidably disposed within a jacket of the flexible instrument. Providing recoverable flexibility to the flexible instrument can include sliding the fluid conduit within the jacket (e.g., using a motorized, controllable slidable mechanism connected to a proximal end portion of the fluid conduit) until a resiliently flexible region of the fluid conduit aligns with the portion of the distal section of the flexible instrument. In yet another embodiment, the sliding element may comprise a stylet. For example, providing recoverable flexibility to the flexible instrument can include inserting and/or sliding a stylet formed of a resiliently flexible material into a lumen of a fluid conduit (e.g., using a motorized, controllable slidable mechanism connected to a proximal end portion of the stylet). In this example, the fluid conduit may be fixedly positioned along the distal section of the flexible instrument while the stylet slidably extends within the fluid conduit.

The method 1600 continues at step 1602 with delivering a distal portion of the flexible instrument at or near a target site within an airway of the patient. As described above, delivering the flexible instrument comprises navigating the complex, tortuous patient anatomy until the distal portion of the flexible instrument is at a desired location, and then orienting the flexible instrument toward the target site or tumor. In some embodiments, delivery of the flexible instrument may be performed manually, the flexible instrument may be robotically controlled by user control through an input device, or the flexible instrument may be robotically controlled automatically using a pre-programmed set of instructions from a robotic system.

At step 1603, once the distal portion of the flexible instrument is positioned and oriented appropriately within the airway, the method 1600 can optionally include delivering a coolant (e.g., a cooling fluid or other cooling agent, such as a gas) or increasing an amount of coolant being delivered to increase rigidity of the flexible instrument. For example, the coolant can be delivered to and/or removed from the channel using a fluid cooling system and/or one or more fluid conduits of the flexible instrument. In some embodiments, delivering the coolant can include delivering the coolant to or removing the coolant from the channel via one or more slots patterned into a fluid conduit.

Coolant delivery may be automatically triggered and controlled by the fluid cooling system based on a detected position of the flexible instrument or may be triggered and controlled based on a user input. For example, the coolant may be automatically delivered when the flexible instrument is detected to have reached the target site or when the flexible instrument has been detected to be oriented towards the target tumor. In another example, the coolant can be delivered through the channel before and/or while positioning the flexible instrument at the target site. In this example, the coolant can be delivered to provide added stiffness to the flexible instrument and/or to prevent the flexible instrument from buckling or kinking during delivery. Accordingly, a volume of coolant may be varied based on the detected position of the flexible instrument through a path to the target. For example, the volume of coolant delivered through the channel can be decreased when the flexible instrument is navigating around tight bends, and/or the volume of coolant delivered through the channel can be increased when the flexible instrument is entering a small diameter structure or when penetrating tissue (as will be described below during step 1604). Additionally, as described in detail below, coolant may also be circulated through the channel to cool the antenna of the flexible instrument. Coolant may also be circulated to dissipate heat from tissue at the target site and/or from the transmission member coupled to the antenna.

At step 1604, the method 1600 includes puncturing an airway wall with a distal end portion of the flexible instrument and positioning an antenna of the flexible instrument at the target site (e.g., within the target tumor or lesion). As explained above, the distal end portion of the flexible instrument must be rigid enough (axially) to puncture tissue without buckling or kinking and can in some examples, be altered to be more rigid using an increase in coolant delivery. In some embodiments, the positioning of the flexible instrument may be performed manually, the flexible instrument may be robotically controlled by user control through an input device, or the flexible instrument may be robotically controlled automatically using a pre-programmed set of instructions from a robotic system.

Once the antenna is positioned within the tumor (or other target tissue), the method 1600 continues at step 1605 with proximal retraction of the sliding element. In some embodiments, for example, the sliding element is the fluid conduit which can be retracted at least until a distal end of the fluid conduit is positioned proximal the proximal end of the antenna such that the fluid conduit does not interfere with the antenna during energy delivery but the fluid conduit remains within the flexible instrument for coolant delivery. In another embodiment, the sliding element is the stylet which can be retracted until the stylet is removed from or at least retracted within the fluid conduit allowing for coolant to be transported via the fluid conduit to a distal portion of the flexible instrument. In some embodiments, the fluid conduit and/or the stylet can be connected to a slidable mechanism (e.g., a controllable mechanism at proximal end portions of the fluid conduit and/or the stylet). In these embodiments, the fluid conduit and/or the stylet can be proximally slid within the jacket using the slidable mechanism. In these and other embodiments, where the fluid conduit is constructed of a shape memory material, the fluid conduit can be proximally retracted within the jacket by applying energy (e.g., thermal energy) to a proximal end portion and/or one or more other portions of the fluid conduit along the length of the fluid conduit (e.g., using a heat source). In some embodiments, retraction of the sliding element may be performed manually, the sliding element may be robotically retracted by user control through an input device, or the sliding element may be robotically retracted automatically based on detection of the antenna within the target tumor.

At step 1606, the method 1600 continues with delivering energy through the transmission member to the antenna (e.g., using a generator electrically coupled to the transmission member) to ablate tissue at the target site (e.g., the tumor), and at step 1607 the method 1600 includes delivering coolant (or continuing/increasing coolant delivery). While in the illustrated embodiment, energy delivery is performed prior to coolant delivery, in various embodiments coolant delivery may be performed prior to energy delivery, or energy delivery and coolant delivery may be performed simultaneously. In various embodiments, rate of energy delivery, delivery flow rate of the coolant, and evacuation flow rate of the coolant can be controlled by operator selection or altered in a closed-loop fashion automatically under control of a computer processor based on sensor feedback (e.g. measured impedance, temperature, imaging information, and/or the like for detection of tissue ablation efficacy). In some embodiments, where the fluid conduit is constructed from shape memory materials, heat generated by the antenna and applied to a portion of the fluid conduit can cause the fluid conduit to contract (e.g., retract, shrink, etc.) proximally within a jacket of the flexible instrument at least until a conductive region of the fluid conduit is positioned proximal the proximal end of the antenna within the jacket. In this embodiment, coolant delivery may be varied to maintain a temperature of the fluid conduit and thus maintain a contraction length of the fluid conduit to a desirable position. Additionally, as mentioned previously and as will be described in more detail below, coolant may be circulated to dissipate heat from tissue at the target site and/or from the transmission member coupled to the antenna.

In some embodiments, the method 1600 may optionally include steps (e.g., steps 1608-1611) for measuring temperature and altering coolant delivery (as necessary) in a closed-loop fashion to maintain a temperature of the antenna preventing overheating and damage to the antenna. At step 1608, for example, the method 1600 may include measuring temperature at or adjacent the antenna and/or the target site. At decision block 1609, if the measured temperature is above a first threshold temperature or range of temperatures (e.g., 110 degrees Celsius to 130 degrees Celsius, or about 120 degrees Celsius), the method 1600 includes increasing coolant delivery (step 1610) and then returning to step 1608 for another temperature measurement. If the measured temperature is not above the first threshold temperature, the method includes maintaining coolant delivery (step 1611) and returning to step 1608. The method continues within a loop returning to step 1608 for another temperature measurement until energy delivery for ablation is complete. As provided above, this closed-loop process is an optional portion of the method 1600 that may not be included in some embodiments of the present technology.

Once ablation is complete (e.g., once tumor/lesion and tissue margins have been adequately ablated as confirmed by sensor feedback such as impedance, temperature, imaging, and/or the like or once a pre-determined period of time has elapsed), the method 1600 continues to step 1612. At step 1612, ablation energy delivery can be terminated, coolant delivery can be terminated, and/or the flexible instrument may be retracted and removed from patient anatomy. In some embodiments where an additional ablation is to be performed at an additional target site, the sliding elements may be repositioned to a fully extended position prior to repositioning of the flexible instrument at a next target site. If no additional targets are to be ablated, however, it may be unnecessary to reposition the sliding elements within the flexible instrument during retraction of the flexible instrument from patient anatomy. In some embodiments, the flexible instrument may be retracted manually, the flexible instrument may be robotically retracted by user control through an input device, or the flexible instrument may be robotically retracted automatically.

Although the steps of the method 1600 are discussed and illustrated in a particular order, the method 1600 illustrated in FIG. 16 is not so limited. In other embodiments, the method 1600 can be performed in a different order. In these and other embodiments, any of the steps of the method 1600 can be performed before, during, and/or after any of the other steps of the method 1600. For example, step 1607 can be performed before, during, and/or after any of the other steps of the method 1600. Moreover, a person of ordinary skill in the relevant art will recognize that the illustrated method 1600 can be altered and still remain within these and other embodiments of the present technology. For example, one or more steps of the method 1600 illustrated in FIG. 16 can be omitted and/or repeated in some embodiments. As a specific example, a flexible instrument in some embodiments can include a fluid conduit (e.g., the fluid conduit 1036 of FIG. 10 or the fluid conduit 1136 of FIG. 11) fixedly positioned within a jacket such that a resiliently flexible region of the fluid conduit is permanently positioned along a portion of the distal section of the antenna instrument. In these embodiments, steps 1601 and 1605 may be omitted. In other embodiments, steps 1603, 1607, 1608, 1609, 1610, and/or 1611 can be omitted.

Figures 17, 18A, 18B:
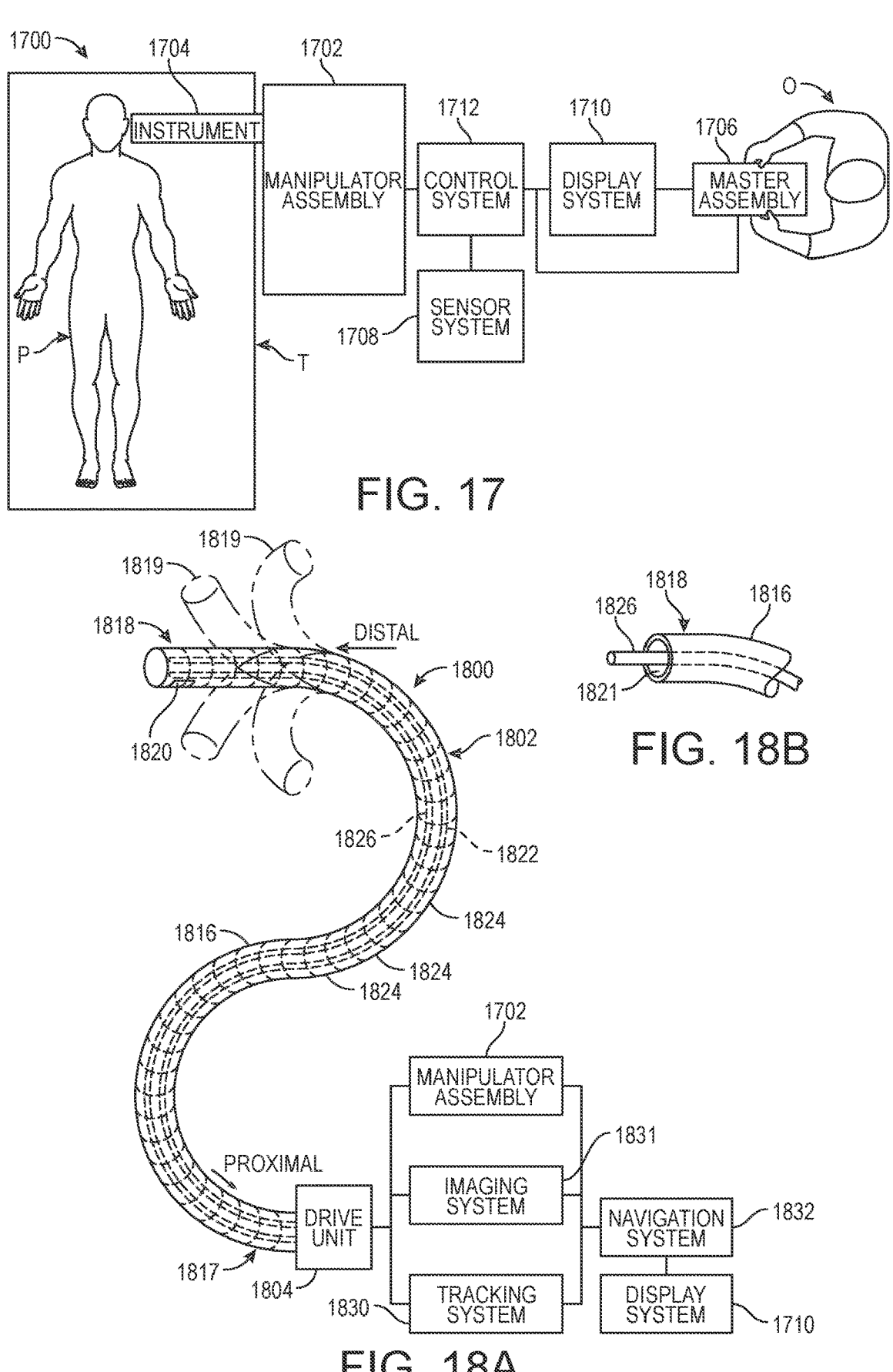
FIG. 17 is a simplified diagram of a teleoperated medical system configured in accordance with various embodiments of the present technology.
FIG. 18A is a simplified diagram of a medical instrument system configured in accordance with various embodiments of the present technology.
FIG. 18B is a simplified diagram of a medical instrument system configured in accordance with various embodiments of the present technology.

While various embodiments, any of the described energy delivery systems may be used as a medical instrument delivered manually, in other embodiments, any of the energy delivery systems may be used as a medical instrument delivered by, coupled to, and/or controlled by a robotic teleoperated and/or non-teleoperated medical system. FIG. 17, for example, is a simplified diagram of a teleoperated medical system 1700 ("medical system 1700") configured in accordance with various embodiments of the present technology. In some embodiments, the medical system 1700 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 17, the medical system 1700 generally includes a manipulator assembly 1702 for operating a medical instrument 1704 in performing various procedures on a patient P positioned on a table T. In some embodiments, the medical instrument 1704 may include, deliver, couple to, and/or control any of the flexible instruments described herein. The manipulator assembly 1702 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated.

The medical system 1700 further includes a master assembly 1706 having one or more control devices for controlling the manipulator assembly 1702. The manipulator assembly 1702 supports the medical instrument 1704 and may optionally include a plurality of actuators or motors that drive inputs on the medical instrument 1704 in response to commands from a control system 1712. The actuators may optionally include drive systems that when coupled to the medical instrument 1704 may advance the medical instrument 1704 into a naturally or surgically created anatomic orifice. Other drive systems may move the distal end of the medical instrument 1704 in multiple degrees of freedom, which may include three degrees of linear motion (e.g., linear motion along the X, Y, and Z Cartesian axes) and in three degrees of rotational motion (e.g., rotation about the X, Y, and Z Cartesian axes). Additionally, the actuators can be used to actuate an articulable end effector of the medical instrument 1704 for grasping tissue in the jaws of a biopsy device and/or the like. Actuator position sensors such as resolvers, encoders, potentiometers, and other mechanisms may provide sensor data to the medical system 1700 describing the rotation and orientation of the motor shafts. This position sensor data may be used to determine motion of the objects manipulated by the actuators.

The medical system 1700 also includes a display system 1710 for displaying an image or representation of the surgical site and the medical instrument 1704 generated by sub-systems of a sensor system 1708 and/or any auxiliary information related to a procedure including information related to ablation (e.g. temperature, impedance, energy delivery power levels, frequency, current, energy delivery duration, indicators of tissue ablation, etc.). The display system 1710 and the master assembly 1706 may be oriented so an operator O can control the medical instrument 1704 and the master assembly 1706 with the perception of tele-presence.

In some embodiments, the medical instrument 1704 may include components of an imaging system, which may include an imaging scope assembly or imaging instrument that records a concurrent or real-time image of a surgical site and provides the image to the operator O through one or more displays of the medical system 1700, such as one or more displays of the display system 1710. The concurrent image may be, for example, a two or three-dimensional image captured by an imaging instrument positioned within the surgical site. In some embodiments, the imaging system includes endoscopic imaging instrument components that may be integrally or removably coupled to the medical instrument 1704. In some embodiments, however, a separate endoscope, attached to a separate manipulator assembly may be used with the medical instrument 1704 to image the surgical site. In some embodiments, the imaging system includes a channel (not shown) that may provide for a delivery of instruments, devices, catheters, and/or the flexible instruments described herein. The imaging system may be implemented as hardware, firmware, software, or a combination thereof which interact with or are otherwise executed by one or more computer processors, which may include the processors of the control system 1712.

The medical system 1700 may also include the control system 1712. The control system 1712 includes at least one memory and at least one computer processor (not shown) for effecting control the between medical instrument 1704, the master assembly 1706, the sensor system 1708, and the display system 1710. The control system 1712 also includes programmed instructions (e.g., a non-transitory machine-readable medium storing the instructions) to implement some or all of the methods described in accordance with aspects disclosed herein, including instructions for providing information to the display system 1710.

The control system 1712 may optionally further include a virtual visualization system to provide navigation assistance to the operator O when controlling the medical instrument 1704 during an image-guided surgical procedure. Virtual navigation using the virtual visualization system may be based upon reference to an acquired preoperative or intra-operative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

FIG. 18A is a simplified diagram of a medical instrument system 1800 configured in accordance with various embodiments of the present technology. The medical instrument system 1800 includes an elongate flexible device 1802, such as a flexible catheter, coupled to a drive unit 1804. The elongate flexible device 1802 includes a flexible body 1816 having a proximal end 1817 and a distal end or tip portion 1818. The medical instrument system 1800 further includes a tracking system 1830 for determining the position, orientation, speed, velocity, pose, and/or shape of the distal end 1818 and/or of one or more segments 1824 along the flexible body 1816 using one or more sensors and/or imaging devices as described in further detail below.

The tracking system 1830 may optionally track the distal end 1818 and/or one or more of the segments 1824 using a shape sensor 1822. The shape sensor 1822 may optionally include an optical fiber aligned with the flexible body 1816 (e.g., provided within an interior channel (not shown) or mounted externally). The optical fiber of the shape sensor 1822 forms a fiber optic bend sensor for determining the shape of the flexible body 1816. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. Pat. No. 7,781,724 (filed Sep. 26, 2006, disclosing "Fiber optic position and shape sensing device and method relating thereto"; U.S. Pat. No. 7,772,541, filed Mar. 12, 2008, titled "Fiber Optic Position and/or Shape Sensing Based on Rayleigh Scatter"; and U.S. Pat. No. 6,389,187, filed Apr. 21, 2000, disclosing "Optical Fiber Bend Sensor," which are all incorporated by reference herein in their entireties. In some embodiments, the tracking system 1830 may optionally and/or additionally track the distal end 1818 using a position sensor system 1820. The position sensor system 1820 may be a component of an EM sensor system with the position sensor system 1820 including one or more conductive coils that may be subjected to an externally generated electromagnetic field. In some embodiments, the position sensor system 1820 may be configured and positioned to measure six degrees of freedom (e.g., three position coordinates X, Y, and Z and three orientation angles indicating pitch, yaw, and roll of a base point) or five degrees of freedom (e.g., three position coordinates X, Y, and Z and two orientation angles indicating pitch and yaw of a base point). Further description of a position sensor system is provided in U.S. Pat. No. 6,380,732, filed Aug. 9, 1999, disclosing "Six-Degree of Freedom Tracking System Having a Passive Transponder on the Object Being Tracked," which is incorporated by reference herein in its entirety. In some embodiments, an optical fiber sensor may be used to measure temperature or force. In some embodiments, a temperature sensor, a force sensor, an impedance sensor, or other types of sensors may be included within the flexible body. In various embodiments, one or more position sensors (e.g. fiber shape sensors, EM sensors, and/or the like) may be integrated within the medical instrument 1826 and used to track the position, orientation, speed, velocity, pose, and/or shape of a distal end or portion of medical instrument 1826 using the tracking system 1830.

The flexible body 1816 includes a channel 1821 sized and shaped to receive a medical instrument 1826. FIG. 18B, for example, is a simplified diagram of the flexible body 1816 with the medical instrument 1826 extended according to some embodiments. In some embodiments, the medical instrument 1826 may be used for procedures such as imaging, visualization, surgery, biopsy, ablation, illumination, irrigation, and/or suction. The medical instrument 1826 can be deployed through the channel 1821 of the flexible body 1816 and used at a target location within the anatomy. The medical instrument 1826 may include, for example, image capture probes, biopsy instruments, laser ablation fibers, and/or other surgical, diagnostic, or therapeutic tools, including any of the flexible instruments (e.g., flexible instruments 100 or 200) or energy delivery systems (e.g., energy delivery systems 300, 400, or 500) described above. The medical instrument 1826 may be used with an imaging instrument (e.g., an image capture probe) within the flexible body 1816. The imaging instrument may include a cable coupled to the camera for transmitting the captured image data. In some embodiments, the imaging instrument may be a fiber-optic bundle, such as a fiberscope, that couples to an image processing system 1831. The imaging instrument may be single or multi-spectral, for example capturing image data in one or more of the visible, infrared, and/or ultraviolet spectrums. The medical instrument 1826 may be advanced from the opening of channel 1821 to perform the procedure and then be retracted back into the channel 1821 when the procedure is complete. The medical instrument 1826 may be removed from the proximal end 1817 of the flexible body 1816 or from another optional instrument port (not shown) along the flexible body 1816.

The flexible body 1816 may also house cables, linkages, or other steering controls (not shown) that extend between the drive unit 1804 and the distal end 1818 to controllably bend the distal end 1818 as shown, for example, by broken dashed line depictions 1819 of the distal end 1818. In some embodiments, at least four cables are used to provide independent "up-down" steering to control a pitch of the distal end 1818 and "left-right" steering to control a yaw of the distal end 1818. Steerable elongate flexible devices are described in detail in U.S. Pat. No. 9,452,276, filed Oct. 14, 2011, disclosing "Catheter with Removable Vision Probe," and which is incorporated by reference herein in its entirety. In various embodiments, medical instrument 1826 (e.g., flexible instruments 100 or 200, or energy delivery systems 300, 400, or 500) may be coupled to drive unit 1804 or a separate second drive unit (not shown) and be controllably or robotically bendable using steering controls.

The information from the tracking system 1830 may be sent to a navigation system 1832 where it is combined with information from the image processing system 1831 and/or the preoperatively obtained models to provide the operator with real-time position information. In some embodiments, the real-time position information may be displayed on the display system 1710 of FIG. 17 for use in the control of the medical instrument system 1800. In some embodiments, the control system 1712 of FIG. 17 may utilize the position information as feedback for positioning the medical instrument system 1800. Various systems for using fiber optic sensors to register and display a surgical instrument with surgical images are provided in U.S. Pat. No. 8,900,131, filed May 13, 2011, disclosing "Medical System Providing Dynamic Registration of a Model of an Anatomic Structure for Image-Guided Surgery," which is incorporated by reference herein in its entirety.

In some embodiments, the medical instrument system 1800 may be teleoperated within the medical system 1700 of FIG. 17. In some embodiments, the manipulator assembly 1702 of FIG. 17 may be replaced by direct operator control. In some embodiments, the direct operator control may include various handles and operator interfaces for hand-held operation of the instrument.

EXAMPLES

Several aspects of the present technology are set forth in the following examples:

1. A flexible instrument, comprising:
an elongate device including an inner conductor, an outer conductor surrounding the inner conductor, and a dielectric layer insulating the inner conductor from the outer conductor;
a recess formed in the outer conductor; and
an insert positioned within the recess and about the inner conductor.

2. The flexible instrument of example 1 wherein the elongate device includes a proximal section and a distal section, and wherein the recess is positioned at the distal section of the elongate device to form an antenna body.

3. The flexible instrument of example 2, further comprising a barrier layer extending over at least a portion of the antenna body and positioned over the insert.

4 The flexible instrument of example 3 wherein the barrier layer includes a plurality of non-conductive layers.

5. The flexible instrument of example 3 or example 4 wherein the barrier layer is configured to secure the insert within the recess.

6. The flexible instrument of example 3 or example 4 wherein one of the plurality of non-conductive layers is configured to seal the antenna body from fluid.

7 The flexible instrument example 3 or example 4 wherein the barrier layer is composed of a fluoropolymer, a plastic material, a heat-shrink material, or a conformal coating.

8. The flexible instrument of any one of examples 1-7, further comprising a jacket layer positioned over at least a portion of the outer conductor.

9 The flexible instrument of example 8, wherein the recess is further formed in the jacket layer.

10. The flexible instrument of example 8 or example 9 wherein the jacket layer is non-conductive.

11. The flexible instrument of any one of examples 8-10 wherein the jacket layer is composed of a plastic material, a PET coating, or a heat-shrink material.

12. The flexible instrument of any one of examples 1-11, further comprising a conductive material electrically coupling the inner conductor to the outer conductor near a distal tip of the flexible instrument.

13. The flexible instrument of any one of examples 1-11, further comprising a conductive material near a distal tip of the flexible instrument and electrically coupled to the inner conductor.

14. The flexible instrument of example 13, further comprising a barrier layer extending over the conductive material, the insert, and over at least a portion of the elongate device.

15. The flexible instrument of example 13, further comprising:
a non-conductive plug formed at a distal end of the conductive material; and
a barrier layer positioned over extending over the conductive material, the non-conductive plug, the insert, and over at least a portion of the elongate device.

16. The flexible instrument of any one of examples 1-15 wherein the insert is a slit tube.

17. The flexible instrument of any one of examples 1-16 wherein the insert is secured within the recess using an adhesive.

18. The flexible instrument of any one of examples 1-17 wherein the insert is non-conductive.

19. The flexible instrument of any one of examples 1-18 wherein the insert fills the recess entirely.

20. The flexible instrument of any one of examples 1-19 wherein the recess has a rectangular, square, trapezoidal, triangular, circular, or oval cross-sectional shape.

21. The flexible instrument of any one of examples 1-19 wherein the recess has a linear, curved, curvilinear, annular, helical, serpentine, or zig-zag shape along a length of the outer conductor.

22. The flexible instrument of any one of examples 1-21 wherein the recess is further formed in the dielectric layer.

23. The flexible instrument of any one of examples 1-22 wherein the outer conductor includes a multi-filament layer.

23. The flexible instrument of any one of examples 1-23 wherein the outer conductor includes at least one of a braided layer, a foil layer, or a nitinol layer.

24. The flexible instrument of any one of examples 1-23 wherein the recess forms a portion of a recess pattern, and wherein the recess pattern includes a first recess and a second recess each formed along a distal section of the outer conductor.

25. The flexible instrument of example 24 wherein the recess pattern is defined by a spacing of the first recess and the second recess, a position of the first recess and the second recess, a shape of the first recess and the second recess, or a size of the first recess and the second recess.

27. The flexible instrument of example 24 wherein:
the insert is a first insert positioned within the first recess; and
the flexible instrument further includes a second insert positioned within the second recess and about the inner conductor.

28. The flexible instrument of any one of examples 1-27 wherein the elongate device includes a proximal section and a distal section, and wherein the proximal section of the elongate device and the distal section of the elongate device are distinct and fixedly coupled cable sections.

29 An energy delivery system, comprising:
the flexible instrument of example 2,
wherein the flexible instrument further comprises—
a transmission member, wherein the antenna body is at a distal end portion of the transmission member;
a sheath surrounding the antenna body and the transmission member; and
at least one fluid conduit at least partially disposed within the sheath, wherein—
the at least one fluid conduit defines a fluid inlet channel configured to transport fluid proximal to a distal end of the antenna body, and
the at least one fluid conduit is configured to provide variable recoverable flexibility along at least a section of the flexible instrument.

30. The system of example 29 wherein the at least one fluid conduit is composed of a material that prevents interference with energy delivery of the antenna body.

31. The system of example 29 or example 30 wherein the at least one fluid conduit includes a first region formed of a resiliently flexible material and a second region formed of a non-conductive material.

32. The system of example 31 wherein the resiliently flexible material is a shape memory material and the non-conductive material is a plastic or a polymer.

33. The system of example 31 or example 32 wherein the first region extends alongside at least a portion of the transmission member within the sheath and terminates at or proximal to the distal end portion of the transmission member.

34. The system of any one of examples 31-33 wherein the at least one fluid conduit further comprises a transition region, wherein the transition region couples the first region to the second region via overlapping or tapering.

35. The system of any one of examples 29-34, further comprising a stylet configured for slidable insertion within the at least one fluid conduit.

36. The system of any one of examples 29-35 wherein the at least one fluid conduit is composed of a non-conductive material and the stylet is formed of a resiliently flexible material.

37. The system of any one of examples 29-36, further comprising a slidable mechanism at a proximal end of the flexible instrument, wherein the slidable mechanism is mechanically coupled to a proximal end portion of the at least one fluid conduit.

38. The system of example 37 wherein the slidable mechanism includes at least one of a linear slide, a cable drive assembly, a robotic arm, or a motor driven leadscrew.

39. The system of any one of examples 29-38 wherein the at least one fluid conduit includes one or more slots or cutouts patterned into the fluid conduit, and wherein at least one slot or cutout of the one or more slots or cutouts is shaped and sized such that fluid exits the at least one fluid conduit into a channel of the flexible instrument about the antenna body.

40. The system of any one of examples 29-38 wherein the at least one fluid conduit includes one or more slots or cutouts patterned into the fluid conduit, and wherein the one or more slots or cutouts is laminated with heat shrink such that the fluid is prevented from exiting the fluid conduit via the slot or cutout.

41. The system of any one of examples 29-40 wherein the at least one fluid conduit includes a first fluid conduit and a second fluid conduit at least partially disposed within the sheath, and wherein a distal end of the first fluid conduit is positioned at a different location along a length of the sheath than a distal end of the second fluid conduit.

42. A method of operating an energy delivery system, the energy delivery system including a flexible instrument having a transmission member, an antenna at a distal end portion of the transmission member, a sheath surrounding the flexible instrument, and a fluid conduit at least partially disposed within the sheath, the method comprising:

providing resilient flexibility, using the fluid conduit, to at least a section of the flexible instrument during navigation of the flexible instrument to a target within a patient;

delivering energy to the target via the antenna; and delivering fluid proximate the antenna at least while delivering energy to the target, wherein the fluid is delivered via the fluid conduit while a distal end of the fluid conduit is extended to a distal end portion of the antenna.

43. The method of example 42 wherein providing resilient flexibility includes using a shape memory material extended to at least the distal end portion of the antenna during the navigation.

44. The method of example 43, further comprising retracting the distal end of the shape memory material to at least the distal end of the transmission member before delivering energy to the target tissue via the antenna.

45. The method of example 43 or example 44 wherein the shape memory material forms a stylet slideably positioned within the fluid conduit, and wherein the fluid conduit is formed of a non-conductive material.

46. The method of any one of examples 43-45 wherein the shape memory material forms the fluid conduit, and wherein the fluid conduit is configured to be slideable within the jacket.

47. An energy delivery system, the system comprising:

a flexible instrument comprising an elongate device having an inner conductor, an outer conductor surrounding the inner conductor, and a dielectric layer insulating the inner conductor from the outer conductor, the flexible instrument further including:

a recess formed in the outer conductor; and an insert disposed within the recess and about the inner conductor;

a sheath surrounding the flexible instrument; and at least one fluid conduit at least partially disposed within the sheath and extending along the flexible instrument, wherein the at least one fluid conduit defines a fluid inlet channel configured to transport fluid to a distal end region of the flexible instrument, and further wherein the at least one fluid conduit provides variable recoverable flexibility along at least a portion of the flexible instrument.

48. The energy delivery system of example 47 wherein the elongate device includes a proximal section and a distal section, and wherein the recess is positioned at the distal section of the elongate device to form an antenna body.

49. The energy delivery system of example 47 or example 48 wherein the insert fills the recess entirely.

50. The energy delivery system of any one of examples 47-49 wherein the recess has a rectangular, square, trapezoidal, triangular, circular, or oval cross-sectional shape.

51. The energy delivery system of any one of examples 47-49 wherein the recess has a linear, curved, curvilinear, annular, helical, serpentine, or zig-zag shape along a length of the outer conductor.

52. The energy delivery system of any one of examples 47-51 wherein the insert is a slit tube.

53. The energy delivery system of any one of examples 47-52 wherein the insert is secured within the recess using an adhesive.

54. The energy delivery system of any one of examples 47-53 wherein the insert is composed of glue, PTFE, FEP, PEEK, or polyurethane.

55. The energy delivery system of any one of examples 47-54, further comprising a stylet configured for slidable insertion within the at least one fluid conduit.

56. The energy delivery system of any one of examples 47-55 wherein the at least one fluid conduit includes a first fluid conduit and a second fluid conduit at least partially disposed within the sheath, and wherein the first fluid conduit runs alongside and is separate from the second fluid conduit.

CONCLUSION

The systems and methods described herein can be provided in the form of tangible and non-transitory machine-readable medium or media (such as a hard disk drive, hardware memory, optical medium, semiconductor medium, magnetic medium, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. Programmed instructions may be implemented as a number of separate programs or subroutines, or they may be integrated into a number of other aspects of the systems described herein. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. In one embodiment, the control system supports wireless communication protocols such as Bluetooth, IrDA, HomeRF, IEEE 802.11, DECT, and Wireless Telemetry. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Medical tools that may be delivered through the elongate flexible devices or catheters disclosed herein may include, for example, image capture probes, biopsy instruments, laser ablation fibers, and/or other surgical, diagnostic, or therapeutic tools. Medical tools may include integrally formed and/or separately attached end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between their proximal and distal ends to controllably bend the distal ends of the tools. Steerable instruments are described in detail in U.S. Pat. No. 7,316,681, filed Oct. 4, 2005, disclosing "Articulated Surgical Instrument for Performing Minimally Invasive Surgery with Enhanced Dexterity and Sensitivity" and U.S. Pat. No. 9,259,274, filed Sep. 30, 2008, disclosing "Passive Preload and Capstan Drive for Surgical Instruments," which are incorporated by reference herein in their entireties.

The systems described herein may be suited for navigation and treatment of anatomic tissues, via natural or surgically created connected passageways, in any of a variety of anatomic systems, including the lung, colon, stomach, intestines, kidneys and kidney calices, bladder, liver, gall bladder, pancreas, spleen, ureter, ovaries, uterus, brain, the circulatory system including the heart, vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A flexible instrument, comprising:
   an elongate device including an inner conductor, an outer conductor surrounding the inner conductor, and a dielectric layer insulating the inner conductor from the outer conductor;
   a non-conductive jacket layer positioned over at least a portion of the outer conductor;
   a recess formed in and extending through a wall of the outer conductor and a wall of the non-conductive jacket layer; and
   an insert positioned within the recess and about the inner conductor.

2. The flexible instrument of claim 1 wherein the elongate device includes a proximal section and a distal section, and wherein the recess is positioned at the distal section of the elongate device to form an antenna body.

3. The flexible instrument of claim 2, further comprising a barrier layer extending over at least a portion of the antenna body and positioned over the insert.

4. The flexible instrument of claim 3 wherein the barrier layer includes a plurality of non-conductive layers.

5. The flexible instrument of claim 4 wherein the barrier layer is configured to secure the insert within the recess or configured to seal the antenna body from fluid.

6. The flexible instrument of claim 1, further comprising a conductive material electrically coupling the inner conductor to the outer conductor near a distal tip of the flexible instrument.

7. The flexible instrument of claim 1, further comprising a conductive material near a distal tip of the flexible instrument and electrically coupled to the inner conductor.

8. The flexible instrument of claim 7, further comprising a barrier layer extending over the conductive material, the insert, and over at least a portion of the elongate device.

9. The flexible instrument of claim 7, further comprising:

a non-conductive plug formed at a distal end of the conductive material; and a barrier layer extending over the conductive material, the non-conductive plug, the insert, and over at least a portion of the elongate device.

10. The flexible instrument of claim 1 wherein the insert is non-conductive.

11. The flexible instrument of claim 1 wherein the recess has a rectangular, square, trapezoidal, triangular, circular, or oval cross-sectional shape.

12. The flexible instrument of claim 1 wherein the recess has a linear, curved, curvilinear, annular, helical, serpentine, or zig-zag shape along a length of the outer conductor.

13. The flexible instrument of claim 1 wherein the recess is further formed in the dielectric layer.

14. The flexible instrument of claim 1 wherein the recess forms a portion of a recess pattern, and wherein the recess pattern includes a first recess and a second recess each formed along a distal section of the outer conductor.

15. The flexible instrument of claim 14 wherein the recess pattern is defined by a spacing of the first recess and the second recess, a position of the first recess and the second recess, a shape of the first recess and the second recess, or a size of the first recess and the second recess.

16. The flexible instrument of claim 14 wherein:

the insert is a first insert positioned within the first recess; and the flexible instrument further includes a second insert positioned within the second recess and about the inner conductor.

17. The flexible instrument of claim 14, wherein the flexible instrument is bendable, and wherein the insert positioned within the recess modifies a bendability of the flexible instrument.

18. The flexible instrument of claim 1 wherein the elongate device includes a proximal section and a distal section, and wherein the proximal section of the elongate device and the distal section of the elongate device are distinct and fixedly coupled cable sections.

19. The flexible instrument of claim 1, wherein the outer conductor includes a braided material and wherein the recess is formed in the braided material.

20. The flexible instrument of claim 1, wherein the recess is one of a plurality of recesses formed in the outer conductor.

* * * * *